US010138522B2

United States Patent
Newman et al.

(10) Patent No.: US 10,138,522 B2
(45) Date of Patent: Nov. 27, 2018

(54) IDENTIFICATION OF CATTLE AT RISK OF HIGH ALTITUDE PULMONARY HYPERTENSION

(71) Applicants: VANDERBILT UNIVERSITY, Nashville, TN (US); COLORADO STATE UNIVERSITY RESEARCH FOUNDATION, Fort Collins, CO (US)

(72) Inventors: John H. Newman, Nashville, TN (US); Rizwan Hamid, Nashville, TN (US); John A. Phillips, Nashville, TN (US); Joy Cogan, Nashville, TN (US); Timothy N. Holt, Fort Collins, CO (US)

(73) Assignees: VANDERBILT UNIVERSITY, Nashville, TN (US); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 96 days.

(21) Appl. No.: 15/121,024

(22) PCT Filed: Jan. 21, 2015

(86) PCT No.: PCT/US2015/012242
§ 371 (c)(1),
(2) Date: Aug. 23, 2016

(87) PCT Pub. No.: WO2015/126557
PCT Pub. Date: Aug. 27, 2015

(65) Prior Publication Data
US 2017/0226583 A1     Aug. 10, 2017

Related U.S. Application Data

(60) Provisional application No. 61/943,651, filed on Feb. 24, 2014.

(51) Int. Cl.
| | | |
|---|---|---|
| *C07H 21/04* | (2006.01) | |
| *C12Q 1/68* | (2018.01) | |
| *C12Q 1/6883* | (2018.01) | |
| *G01N 33/53* | (2006.01) | |
| *C07K 16/28* | (2006.01) | |

(52) U.S. Cl.
CPC ............ *C12Q 1/6883* (2013.01); *C07K 16/28* (2013.01); *G01N 33/5308* (2013.01); *C07K 2317/34* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS 5,695,963 A    12/1997  McKnight et al.
2012/0258878 A1 10/2012  Saad

OTHER PUBLICATIONS

Heaton et al. (F1000Research, vol. 5, pp. 1-23, Feb. 7, 2018) (Year: 2018).*
Bovine HD Genotyping BeadChip,Data Sheet. Illunnina, 2010. (Year: 2010).*
Gene Chip Bovine Genome Array, Data Sheet, Affymetrix, 2011. (Year: 2011).*
Genbank Accession No. NM_174725.2, Bos Taurs endothelial PAS domain protein (EPAS1), mRNA, May 14, 2018. (Year: 2018).*
Beall, Cynthia M et al. "Natural selection on EPAS1 (HIF2α) associated with low hemoglobin concentration in Tibetan highlanders." Proceedings of the National Academy of Sciences 107.25 (2010): 11459-11464.
Bryan, "Bovine High Altitude Disease Studied in New Mexico Cattle", *Huff Post Green*, dated Oct. 3, 2011.
Gale, Daniel P., et al. "Autosomal dominant erythrocytosis and pulmonary arterial hypertension associated with an activating HIF2α mutation." Blood 112.3 (2008): 919-921.
Gjermundson, C. K. "Danger at 5,000 feet." *Angus J* (2000): 47-50.
Hickey, Michele M., et al. "The von Hippel-Lindau Chuvash mutation promotes pulmonary hypertension and fibrosis in mice." The Journal of clinical investigation 120.3 (2010): 827-839.
International Preliminary Report on Patentability issued in International Application No. PCT/US15/12242, dated Sep. 9, 2016.
International Search Report and Written Opinion issued in International Application No. PCT/US15/12242, dated May 14, 2015.
Newman et al. "High-altitude pulmonary hypertension of peripheral blood in cattle (brisket disease): candidate genes and gene expression profiling of peripheral blood mononuclear cells." *Pulmonary Circulation* 1.4(2011): 462.
Percy, Melanie J., et al. "A gain-of-function mutation in the HIF2A gene in familial erythrocytosis." New England Journal of Medicine 358.2 (2008): 162-168.
Simonson, Tatum S., et al. "Genetic evidence for high-altitude adaptation in Tibet." Science 329.5987 (2010): 72-75.
Tan, Qiulin, et al. "Erythrocytosis and pulmonary hypertension in a mouse model of human HIF2A gain of function mutation." Journal of Biological Chemistry 288.24 (2013): 17134-17144.

(Continued)

*Primary Examiner* — Jeanine A Goldberg
(74) *Attorney, Agent, or Firm* — Parker Highlander PLLC

(57) ABSTRACT

Provided herein are methods and compositions for determining the susceptibility of cattle to High Altitude Pulmonary Hypertension. Also provide are kits and reagents for performing such methods.

12 Claims, 5 Drawing Sheets
Specification includes a Sequence Listing.

(56) References Cited

OTHER PUBLICATIONS

UniProtKB Accession No. A5PJT1_BOVIN—Endothelial PAS domain protein 1, dated Jul. 10, 2007.
Weir, E. K., et al. "The genetic factor influencing pulmonary hypertension in cattle at high altitude1." (1974).
West et al. "High-altitude medicine." *American journal of respiratory and critical care medicine* 196.12 (2012): 1229-1237.
Yi, Xin, et al. "Sequencing of 50 human exomes reveals adaptation to high altitude." science 329.5987 (2010): 75-78.

* cited by examiner

EPAS1 (HIF2α)

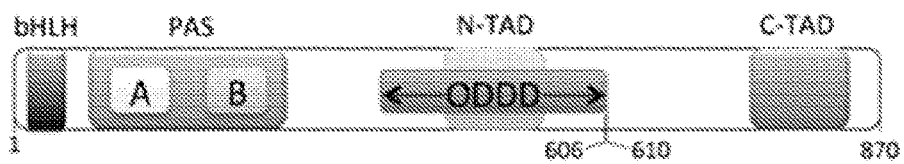

FIG. 8

| | | | |
|---|---|---|---|
| B Taurus with High PAP | | ...TPT...GSRVSLLQCCGQTYTPLSSMGGISNTQWPPDPPLQLGPTKWPGS | (SEQ ID NO 1) |
| B Taurus | NP_777150 | APT...GSRVSLLQCCGQTYTPLSSMGGISNTQWPPDPPLQLGPTKWPGS | (SEQ ID NO 2) |
| B Grunniens | ENSP00009263734 | APT...GSRVSLLQCCGQTYTPLSSMGGISNTQWPPDPPLQLGPTKWPGS | (SEQ ID NO 3) |
| H Sapien | NP_001421 | LPT...SKASLPPCCGQASTPLSSMGGRSNTQWPPDPPLRFGPTRWAVG | (SEQ ID NO 4) |
| M Musculus | NP_034267 | LPT...SKGSLSPCCGQASTPLSSMGGRSNTQWPPDPPLRFGPTRWPVG | (SEQ ID NO 5) |
| R Norvegicus | NP_075578 | LPT...SKGSLPPCCGQASTPLSSMGGRSNTPWPDPPLRLGPTRWSVG | (SEQ ID NO 6) |
| P Troglodytes | XP_001147219 | LPT...SKASLPPCCGQASTPLSSMGGRSNTQWPPDPPLRFGPTRWAVG | (SEQ ID NO 7) |
| O Aries | ENSOART00000006234 | TPT...GSRVSLLQCCGQTYTPLSSMGGISSTQWPPDPPLQLGPRKWPGS | (SEQ ID NO 8) |

FIG. 9

```
                          SEQUENCE LISTING

<160> NUMBER OF SEQ ID NOS: 8

<210> SEQ ID NO 1
<211> LENGTH: 49
<212> TYPE: PRT
<213> ORGANISM: Artificial Sequence
<220> FEATURE:
<223> OTHER INFORMATION: Synthetic peptide

<400> SEQUENCE: 1

Thr Phe Phe Asp Ser Gly Ser Arg Val Ser Leu Leu Gln Cys Cys Gly
1               5                   10                  15

Gln Thr Tyr Thr Pro Leu Ser Ser Met Gly Gly Ile Ser Asn Thr Gln
            20                  25                  30

Trp Pro Pro Asp Pro Pro Leu Gln Leu Gly Pro Thr Lys Trp Pro Gly
        35                  40                  45

Glu

<210> SEQ ID NO 2
<211> LENGTH: 49
<212> TYPE: PRT
<213> ORGANISM: Artificial Sequence
<220> FEATURE:
<223> OTHER INFORMATION: Synthetic peptide

<400> SEQUENCE: 2

Ala Phe Phe Asp Gly Gly Ser Arg Val Ser Leu Leu Gln Cys Cys Gly
1               5                   10                  15

Gln Thr Tyr Thr Pro Leu Ser Ser Met Gly Gly Ile Ser Asn Thr Gln
            20                  25                  30

Trp Pro Pro Asp Pro Pro Leu Gln Leu Gly Pro Thr Lys Trp Pro Gly
        35                  40                  45

Glu

<210> SEQ ID NO 3
<211> LENGTH: 49
<212> TYPE: PRT
<213> ORGANISM: Artificial Sequence
<220> FEATURE:
<223> OTHER INFORMATION: Synthetic peptide

<400> SEQUENCE: 3

Ala Phe Phe Asp Gly Gly Ser Arg Val Ser Leu Leu Gln Cys Cys Gly
1               5                   10                  15

Gln Thr Tyr Thr Pro Leu Ser Ser Met Gly Gly Ile Ser Asn Thr Gln
            20                  25                  30

Trp Pro Pro Asp Pro Pro Leu Gln Leu Gly Pro Thr Lys Trp Pro Gly
        35                  40                  45

Glu

<210> SEQ ID NO 4
<211> LENGTH: 49
<212> TYPE: PRT
<213> ORGANISM: Artificial Sequence
<220> FEATURE:
<223> OTHER INFORMATION: Synthetic peptide
```

<400> SEQUENCE: 4

Ile Phe Phe Asp Ala Gly Ser Lys Ala Ser Leu Pro Pro Cys Cys Gly
1               5                   10                  15

Gln Ala Ser Thr Pro Leu Ser Ser Met Gly Gly Arg Ser Asn Thr Gln
            20                  25                  30

Trp Pro Pro Asp Pro Pro Leu His Phe Gly Pro Thr Lys Trp Ala Val
        35                  40                  45

Gly

<210> SEQ ID NO 5
<211> LENGTH: 49
<212> TYPE: PRT
<213> ORGANISM: Artificial Sequence
<220> FEATURE:
<223> OTHER INFORMATION: Synthetic peptide

<400> SEQUENCE: 5

Ile Phe Phe Asp Ala Gly Ser Lys Gly Ser Leu Ser Pro Cys Cys Gly
1               5                   10                  15

Gln Ala Ser Thr Pro Leu Ser Ser Met Gly Gly Arg Ser Asn Thr Gln
            20                  25                  30

Trp Pro Pro Asp Pro Pro Leu His Phe Gly Pro Thr Lys Trp Pro Val
        35                  40                  45

Gly

<210> SEQ ID NO 6
<211> LENGTH: 49
<212> TYPE: PRT
<213> ORGANISM: Artificial Sequence
<220> FEATURE:
<223> OTHER INFORMATION: Synthetic peptide

<400> SEQUENCE: 6

Ile Phe Phe Asp Ala Gly Ser Lys Gly Ser Leu Pro Pro Cys Cys Gly
1               5                   10                  15

Gln Ala Ser Thr Pro Leu Ser Ser Met Gly Gly Arg Ser Asn Thr Pro
            20                  25                  30

Trp Pro Pro Asp Pro Pro Leu His Leu Gly Pro Thr Lys Trp Ser Val
        35                  40                  45

Gly

<210> SEQ ID NO 7
<211> LENGTH: 49
<212> TYPE: PRT
<213> ORGANISM: Artificial Sequence
<220> FEATURE:
<223> OTHER INFORMATION: Synthetic peptide

<400> SEQUENCE: 7

Ile Phe Phe Asp Ala Gly Ser Lys Ala Ser Leu Pro Pro Cys Cys Gly
1               5                   10                  15

Gln Ala Ser Thr Pro Leu Ser Ser Met Gly Gly Arg Ser Asn Thr Gln
            20                  25                  30

Trp Pro Pro Asp Pro Pro Leu His Phe Gly Pro Thr Lys Trp Ala Val
        35                  40                  45

Gly

<210> SEQ ID NO 8

```
<211> LENGTH: 49
<212> TYPE: PRT
<213> ORGANISM: Artificial Sequence
<220> FEATURE:
<223> OTHER INFORMATION: Synthetic peptide

<400> SEQUENCE: 8

Thr Phe Phe Asp Gly Gly Ser Lys Val Ser Leu Leu Gln Arg Cys Gly
1               5                   10                  15

Gln Thr Tyr Thr Pro Leu Ser Ser Met Gly Gly Ile Ser Ser Thr Gln
            20                  25                  30

Trp Pro Pro Asp Pro Pro Leu Gln Leu Gly Pro Met Lys Trp Pro Gly
        35                  40                  45

Glu
```

IDENTIFICATION OF CATTLE AT RISK OF HIGH ALTITUDE PULMONARY HYPERTENSION

This application is a national phase application under 35 U.S.C. § 371 of International Application No. PCT/US2015/012242, filed Jan. 21, 2015, which claims benefit of priority to U.S. Provisional Application Ser. No. 61/943,651, filed Feb. 24, 2014, the entire contents of each of which are hereby incorporated by reference.

BACKGROUND OF THE INVENTION

1. Field of the Invention

The present invention relates generally to the fields of agriculture, genetics, and veterinary medicine. More particularly, it concerns identifying cattle at risk of High Altitude Pulmonary Hypertension (HAPH).

2. Description of Related Art

High mountain disease (brisket disease) is right heart failure due to pulmonary hypertension in cattle residing at high altitude. Pulmonary hypertension is defined as mean pressure in the pulmonary circulation greater than 25 mmHg. If pulmonary hypertension is severe or prolonged, the right ventricle is unable to pump effectively and heart failure ensues with loss of the animal.

Hypoxia is the most potent stimulus for pulmonary hypertension and the hypoxia of high altitude (>7000 ft) is a well known cause. Some cattle (*Bos taurus*) have a genetic susceptibility to severe high altitude pulmonary hypertension (HAPH) that is heritable. While most cattle thrive at high altitude, susceptible cattle develop pulmonary hypertension that is sufficient to cause right heart failure, edema of the brisket, and death. Experiments in the 1970's using cross breeding of susceptible cattle with cattle resistant to HAPH strongly point to an autosomal dominant mode of inheritance, possibly of a single major causative gene. No information exists on what gene may have mutations or functional polymorphisms that cause this exaggerated response.

HAPH in cattle occurs in about 15% of animals brought to high altitude (>7000 ft) to replenish herds, and costs ranchers millions of dollars of lost income each year. If the causative HAPH gene cold be discovered by analysis of DNA from HAPH and hypoxia resistant cattle living at high altitude, this could provided the basis for screening of animals that cannot tolerate high altitude and their removal from that environment. It is also possible that the gene responsible for HAPH is involved in pulmonary hypertension in humans, further increasing the value of such a correlation.

SUMMARY OF THE INVENTION

Thus, in accordance with the present disclosure, there is provided a method of identifying cattle having or at risk of High Altitude Pulmonary Hypertension (HAPH) comprising (a) subjecting a nucleic acid containing sample from a head of cattle to sequence analysis; (b) determining the presence or absence of (i) an G→A transition at position c. 1816 in exon 12 of the EPAS1 gene (NM_174725) and/or (ii) a G→A transition at position c. 1828 in exon 12 of the EPAS1 gene (NM_174725); and (c) identifying said head of cattle has having or at risk of HAPH when one or both of said transitions occur. The method may further comprise transporting said head of cattle out of a high altitude environment if one or both of said transitions occur, or further comprise transporting said head of cattle from a low altitude environment to a high altitude environment if neither of said transitions occur. The method may also further comprise not breeding said head of cattle if one or both of said transitions occur, or further comprise breeding said head of cattle if neither of said transitions does not occur, such as by artificial insemination.

The nucleic acid containing sample may be is a DNA sample or an RNA sample. The nucleic acid containing sample may be a tissue, saliva, serum, blood, semen, ova, hair or a mucosal cell. The sequence analysis may comprise PCR, primer extension, site specific amplification, site specific hybridization, site specific cleavage, ligation, pyrosequencing, SNP microarray, minisequencing, RNA seq, real time sequencing, and/or ion torrent pH sensing. The head of cattle is *Bos taurus* or *Bos primigenius*.

The method may further comprise subjecting said nucleic acid-containing sample to analysis of expression of one or more of:

Angiogenin, ribonuclease, Rnase A family, 5
BCL2/adenovirus E1B 19 kDa interacting protein 3-like
Cell adhesion molecule 1
CD59 molecule, complement regulatory protein
CYB5 protein
Dual specificity phosphatase 1
Endothelin converting enzyme 1
FBJ murine osteosarcoma viral oncogene homolog
Growth arrest and DNA-damage-inducible, beta
Glycogen synthase 1 (muscle)
Interferon stimulated exonuclease gene 20 kDa
Jun oncogene
Kruppel-like factor 6
N-myc downstream regulated 1
Nuclear factor, interleukin 3 regulated
Peptidylglycine alpha-amidating monooxygenase
6-phosphofructo-2-kinase/fructose-2,6-biphosphatase 3
Placenta-specific 8
Plasminogen activator, urokinase receptor
S100 calcium binding protein A4
Spermidine/spermine N1-acetyltransferase 1
Scavenger receptor class B, member 1
Serpin peptidase inhibitor, clade E
Sortilin-related receptor, L(DLR class) A repeats-containing
Thioredoxin interacting protein
Very low density lipoprotein receptor
and
Zinc finger, MYND-type containing 8.

In another embodiment, there is provided a method of identifying cattle having or at risk of High Altitude Pulmonary Hypertension (HAPH) comprising (a) subjecting a protein containing sample from a head of cattle to sequence analysis; (b) determining the presence or absence of (i) an Ala→Thre substitution at residue 606 in exon 12 of EPAS1 (NP_777150.1) and/or (ii) a Gly→Ser substitution at residue 610 in exon 12 of EPAS1 (NP_777150.1); and (c) identifying said head of cattle has having or at risk of HAPH when one or both of said substitutions occur. The method may further comprise transporting said head of cattle out of a high altitude environment if one or both of said substitutions occur, or further comprise transporting said head of cattle from a low altitude environment to a high altitude environment if neither of said substitutions occur. The method may also further comprise not breeding said head of cattle if one or both of said substitutions occur, or further comprise breeding said head of cattle if neither of said substitutions occur, such as by artificial insemination.

The protein containing sample may be a tissue sample, blood, hair, serum, ova, a mucosal cell, urine, stool, saliva or semen. The sequence analysis may be an antibody-based assay or mass spectrometry. The head of cattle any know breed, may be *Bos taurus* or *Bos primigenius*, and in particular may be black angus, Hereford, red angus, simmental, limousine, balancer, stabilizer, south Devon, galloway, black irish and all known miniature breeds of cattle.

The method may further comprise subjecting said protein-containing sample to analysis of expression of one or more of:

Angiogenin, ribonuclease, Rnase A family, 5
BCL2/adenovirus E1B 19 kDa interacting protein 3-like
Cell adhesion molecule 1
CD59 molecule, complement regulatory protein
CYB5 protein
Dual specificity phosphatase 1
Endothelin converting enzyme 1
FBJ murine osteosarcoma viral oncogene homolog
Growth arrest and DNA-damage-inducible, beta
Glycogen synthase 1 (muscle)
Interferon stimulated exonuclease gene 20 kDa
Jun oncogene
Kruppel-like factor 6
N-myc downstream regulated 1
Nuclear factor, interleukin 3 regulated
Peptidylglycine alpha-amidating monooxygenase
6-phosphofructo-2-kinase/fructose-2,6-biphosphatase 3
Placenta-specific 8
Plasminogen activator, urokinase receptor
S100 calcium binding protein A4
Spermidine/spermine N1-acetyltransferase 1
Scavenger receptor class B, member 1
Serpin peptidase inhibitor, clade E
Sortilin-related receptor, L(DLR class) A repeats-containing
Thioredoxin interacting protein
Very low density lipoprotein receptor
and
Zinc finger, MYND-type containing 8.

In yet another embodiment, there is provided a kit comprising (a) a first nucleic acid probe or primer for determining the presence or absence of a G→A transition at position c. 1816 in exon 12 of the EPAS1 gene (NM_174725); (b) a second nucleic acid probe or primer for determining the presence or absence of a G→A transition at position c. 1828 in exon 12 of the EPAS1 gene (NM_174725). The kit may further comprise one or more of a polymerase, a ligase, a restriction enzyme, a buffer, instructions for use of said kit, or a label. The kit may also further comprise one or more containers for storage of said probe or primers. The kit may further comprise one or more nucleic acid probes or primers for assessing the level of an mRNA encoding:

Angiogenin, ribonuclease, Rnase A family, 5
BCL2/adenovirus E1B 19 kDa interacting protein 3-like
Cell adhesion molecule 1
CD59 molecule, complement regulatory protein
CYB5 protein
Dual specificity phosphatase 1
Endothelin converting enzyme 1
FBJ murine osteosarcoma viral oncogene homolog
Growth arrest and DNA-damage-inducible, beta
Glycogen synthase 1 (muscle)
Interferon stimulated exonuclease gene 20 kDa
Jun oncogene
Kruppel-like factor 6
N-myc downstream regulated 1
Nuclear factor, interleukin 3 regulated
Peptidylglycine alpha-amidating monooxygenase
6-phosphofructo-2-kinase/fructose-2,6-biphosphatase 3
Placenta-specific 8
Plasminogen activator, urokinase receptor
S100 calcium binding protein A4
Spermidine/spermine N1-acetyltransferase 1
Scavenger receptor class B, member 1
Serpin peptidase inhibitor, clade E
Sortilin-related receptor, L(DLR class) A repeats-containing
Thioredoxin interacting protein
Very low density lipoprotein receptor
and/or
Zinc finger, MYND-type containing 8.

In still yet another embodiment, there is provided a kit comprising (a) a first antibody for determining the presence or absence of an Ala→Thr substitution at residue 606 in exon 12 of EPAS1 (NP_777150.1); (b) a second antibody for determining the presence or absence of a Gly→Ser substitution at residue 610 in exon 12 of EPAS1 (NP_777150.1). The kit may further comprise one or more of a support, a third antibody for detection of said first and/or second antibody, a buffer, instructions for use of said kit, or a label. The kit may also further comprise one or more containers for storage of said antibodies.

In a further embodiment, there is provided a probe or primer having a sequence that hybridizes to or adjacent to c. 1816 of EPAS1 (NM_174725); a probe or primer having a sequence that hybridizes to or adjacent to c. 1828 of EPAS1 (NM_174725); a probe or primer having a sequence that hybridizes to c. 1816 and c. 1828 of EPAS1 (NM_174725); an antibody that binds selectively to an epitope comprising residue 606 of EPAS1 (NP_777150.1); or an antibody that binds selectively to an epitope comprising residue 610 of EPAS1 (NP_777150.1).

The antibody kits of the two preceding paragraphs may further comprise one or more antibodies that bind immunologically to:

Angiogenin, ribonuclease, Rnase A family, 5
BCL2/adenovirus E1B 19 kDa interacting protein 3-like
Cell adhesion molecule 1
CD59 molecule, complement regulatory protein
CYB5 protein
Dual specificity phosphatase 1
Endothelin converting enzyme 1
FBJ murine osteosarcoma viral oncogene homolog
Growth arrest and DNA-damage-inducible, beta
Glycogen synthase 1 (muscle)
Interferon stimulated exonuclease gene 20 kDa
Jun oncogene
Kruppel-like factor 6
N-myc downstream regulated 1
Nuclear factor, interleukin 3 regulated
Peptidylglycine alpha-amidating monooxygenase
6-phosphofructo-2-kinase/fructose-2,6-biphosphatase 3
Placenta-specific 8
Plasminogen activator, urokinase receptor
S100 calcium binding protein A4
Spermidine/spermine N1-acetyltransferase 1
Scavenger receptor class B, member 1
Serpin peptidase inhibitor, clade E
Sortilin-related receptor, L(DLR class) A repeats-containing Thioredoxin interacting protein
Very low density lipoprotein receptor
and
Zinc finger, MYND-type containing 8.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8. Graphic depiction of the known EPAS1 domains. bHLH: basic Helix-Loop-Helix, PAS: Per-Arnt-Sim domain, ODDD: Oxygen Dependent Degradation Domain, N-TAD: N-Terminal Transactivation Domain, C-TAD: C-Terminal Transactivation Domain. The two variants are in the ODDD domain of the protein.

FIG. 9. Amino acid sequence alignment of the HIF2a segment containing the double variant in multiple species. Variants are in bold. The double variant has not been found in *B. grunniens* (Yak) (n=1) which is adapted to high altitude. One of the two variants has been reported in *O Aires* (sheep). NP or ESN numbers represent reference protein sequence in NCBI or Ensembl databases.

DESCRIPTION OF ILLUSTRATIVE EMBODIMENTS

Figure 1:
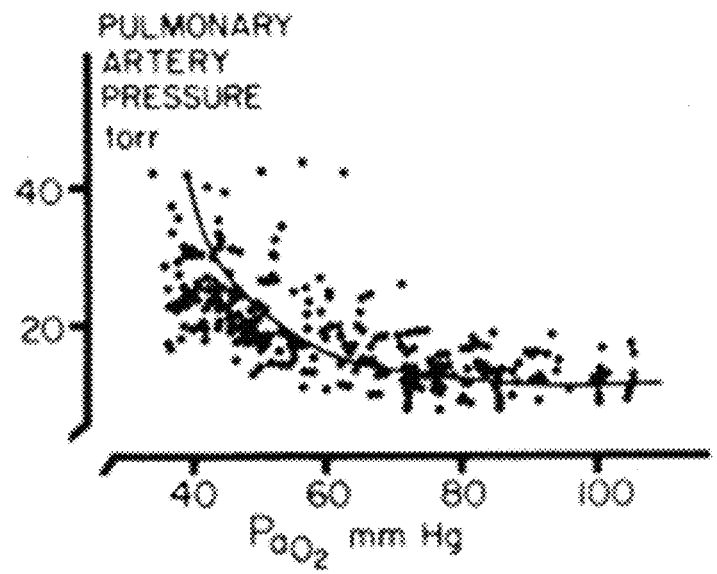
FIG. 1. Pulmonary response as a function of $PO_2$ in *Homo sapiens*.

There are several million cattle at risk of HAPH in the high country of the United States, and the annual losses in stock amount to multi-millions of dollars. To date, no major genetic variants have been identified that modify the strength of the hypoxic pressor response (Pasha and Newman, 2010). Some observations have been made regarding genetic associations with pulmonary responses to altitude in humans. For example, eNOS and tyrosine kinase gene variants were overrepresented in a Japanese cohort of individuals suspectible to HAPE as compared with healthy controls at altitude (Droma et al., 2002; Hanaoka et al., 2003). Others have detected an association between the LL genotype of the human SLC6A4 (formerly SERT) with pulmonary artery pressure in a cohort of patients with chronic obstructive pulmonary disease as compared with controls (Eddahibi et al., 2003). Recent studies implicate a HIF-2α polymorphism in Tibetan versus Han as a possible difference in successful high-altitude adaptation. Many other signaling pathways possess potential candidate genes (Rabinovitch, 2005).

The present application describes the discovery of a causal gene and the functional polymorphisms in breeds at risk of HAPH so that testing, breeding and preventive herd management can be implemented. Such a test for cattle and herds intended to move to high altitudes and of bull sperm sent to altitude for insemination could provide considerable cost savings to those in the industry. These and other details of the disclosure are described below.

I. DEFINITIONS

As used herein, an "allele" is one of a pair or series of genetic variants of a polymorphism at a specific genomic location. A "response allele" is an allele that is associated with altered response to a treatment. Where a SNP is biallelic, both alleles will be response alleles (e.g., one will be associated with a positive response, while the other allele is associated with no or a negative response, or some variation thereof).

As used herein, "genotype" refers to the diploid combination of alleles for a given genetic polymorphism. A homozygous subject carries two copies of the same allele and a heterozygous subject carries two different alleles.

As used herein, a "haplotype" is one or a set of signature genetic changes (polymorphisms) that are normally grouped closely together on the DNA strand, and are inherited as a group; the polymorphisms are also referred to herein as "markers." A "haplotype" as used herein is information regarding the presence or absence of one or more genetic markers in a given chromosomal region in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., a CA nucleotide pair repeated three times), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Copy number variation" (CNV), as used herein, refers to variation from the normal diploid condition for a gene or polymorphism. Individual segments of human chromosomes can be deleted or duplicated such that the subject's two chromosomes carry fewer than two copies of the gene or polymorphism (a deletion or deficiency) or two or more copies (a duplication).

"Linkage disequilibrium" (LD) refers to when the observed frequencies of haplotypes in a population does not agree with haplotype frequencies predicted by multiplying together the frequency of individual genetic markers in each haplotype. When SNPs and other variations that comprise a given haplotype are in LD with one another, alleles at the different markers correlate with one another.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "high altitude" as used herein refers to elevations above 5000 feet above sear level. The HAPH response is not linear with increasing altitude and is worse above 7000 ft. Between 3000 and 5000 ft, some cattle develop pulmonary hypertension, and this may be referred to an a "intermediate altitude."

The term "low altitude" as used herein refers to elevations above sea level less than below 3000 ft.

The term "pulmonary hypertension" as used herein refers to mean pulmonary arterial pressure greater than 40 mmHg.

The term "gene" refers to a DNA sequence in a chromosome that encodes a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing the same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of the hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably, at least partially, single stranded (e.g., denatured) at the time of hybridization. When the target nucleotide sequences are located only in a single region or fraction of a given chromosome, the term "target region" is sometimes used. Targets for hybridization can be derived from specimens that include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., Current Protocols in Molecular Biology, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

The term "SNP" stands for single nucleotide polymorphism, and in particular refers to SNPs located at positions 28662654 and 28662666 of bovine chromosome 11 in exon 12 of the EPAS1 gene.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30% (e.g., at least 40%, 50%, 60%, 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80% (e.g., 85%, 90%, 95%, 97% or more) identical.

The term "nonspecific binding DNA" refers to DNA that is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or alleles described herein. The stratification can be performed, e.g., in the course of analysis, or can be used in creation of distinct groups or in other ways.

II. HIGH ALTITUDE PULMONARY HYPERTENSION

Hypoxic pulmonary vasoconstriction, followed by muscularization of the pulmonary arterioles and pre-capillary vessels, is the cause of pulmonary hypertension in a large number of conditions and diseases in humans and animals (Moudgil et al., 2005, Palevsky and Fishman, 1990, Nocturnal Oxygen Therapy Trial Group. Ann Intern Med 1980, Peacock and Rubin, 2004 and Richards, 1966). These range from hypoventilation syndromes (Atwood et al., 2004 and Chaouat et al., 1996), to diseases of ventilation-perfusion mismatch, especially emphysema (Nocturnal Oxygen Therapy Trial Group. Ann Intern Med 1980, Chaouat et al., 1996, MacNee, 1994 and Weitzenblum et al., 1981) to neuromuscular diseases (Fanburg et al., 1994) and to high altitude illnesses (Heath and William, 1981, Reeves and Grover, 2004, Grover, 1965 and Maggiorini and Leon-Velarde, 2003). In diseases that interfere with oxygenation and ventilation, the major characteristic that determines the pulmonary response to hypoxia is hypoxic pulmonary vasoconstriction, in which small pulmonary arterioles constrict in response to lung hypoxia (Moudgil et al., 2005, Stenmark and McMurtry, 2005 and Sylvester, 2001).

Hypoxic pulmonary vasoconstriction was first discovered by von Euler and Liljestrand in 1946 (von Euler and Liljestrand, 1946). They correctly surmised that focal hypoxic vasoconstriction might function to improve oxygenation by diverting blood from poorly ventilated regions of lung, but that generalized hypoxic vasoconstriction could lead to elevated pulmonary arterial pressure. Despite over sixty years of effort, the exact mechanism causing acute hypoxic vasoconstriction remains elusive, although much is known about modifying influences (Moudgil et al., 2005, Stenmark and McMurtry, 2005, Sylvester, 2001 and Weissmann et al., 2001). Hypoxic vasoconstriction relies on calcium entry into smooth muscle cells, and on activation of actin filaments (Moudgil et al., 2005, Ward and Robertson, 2005, Mauban et al., 2005 and Wang et al., 2003). K channel function has a central role, as does oxidant stress (Moudgil et al., 2005, Mauban et al., 2005, Mauban et al., 2005, Remillard and Yuan, 2005 and Wolin et al., 2005). Rho-RhoKinases are involved in transduction of the hypoxic pressor response (Wang et al., 2003, Fagan et al., 2004, Nagaoka et al., 2004, Jernigan et al., 2004 and Wood, 1958).

Marked differences exist among individuals and among species in the response of the pulmonary vascular bed to left heart dysfunction, and to shear stress through alterations in pressure and flow and thus may also have a genetic basis (Jernigan et al., 2004). No major genes have been identified that determine the strength of the hypoxic pressor response. However, multiple observations have confirmed that inherited variation in ventilatory responses and the hypoxic pressor response have major effects on pulmonary artery dynamics (Heath and William, 1981, Fagan and Weil, In Press and Mortimer et al., 2004). Pulmonary pressures in normal humans living at low and high altitude are shown in FIG. 1 (Grover et al., 1983 and Fishman, 1985). Pulmonary hypertension does not occur until the partial pressure of oxygen in the atmosphere ($PO_2$) decreases into the range of 50-60 mmHg, consistent with the steep portion of the oxy-hemoglobin dissociation curve. In man racial differences may underliesome of the responses to high altitude exposure (Heath and William, 1981, Reeves and Grover, 2004, Fagan and Weil, In Press, Mortimer et al., 2004, Grover, 1965, Morrell et al., 2003, Rupert and Hochachka, 2001, Rhodes, 2005 and Moore et al., 2000). Chronic high altitude pulmonary hypertension is rare in the Tibetan Sherpa, but more common in the Quechua of the Andes (Groves et al., 1993 and Rupert and Hochachka, 2001). Numerous physiological studies have been unable to clearly separate high altitude responses in these two populations, but part of the evidence is that the Sherpa has a more responsive ventilatory response to hypoxia and may be protected at high altitudes during exercise and perhaps during sleep (Reeves and Grover, 2004, Fagan and Weil, In Press and Mortimer et al., 2004). The evidence in cattle is that chronic hypoxic pulmonary hypertension is not related to ventilatory responses (Weir et al., 1974). Few observations have been made on genetic associations of pulmonary responses to altitude and COPD in humans. Hanaoka et al. found a prevalence of the Glu298Asp variant in the NOS3 gene in 25% of high altitude pulmonary edema (HAPE) susceptible but only 7% of controls (Droma et al., 2002) and an association with HLA-DR6 and tyrosine kinases (Hanaoka et al., 2003). Eddahabi and Adnot have found an association of LL genotype of the serotonin transporter (SERT) with pulmonary artery pressure in a cohort of patients with chronic bronchitis and emphysema, 34+/−3 versus 22+/−2 mmHg in SS or SL genotype, respectively (Eddahibi et al., 2003). The LL genotype is expected to increase intracellular serotonin. This field is young and inheritance of susceptibility is only recently being addressed.

Figure 2:
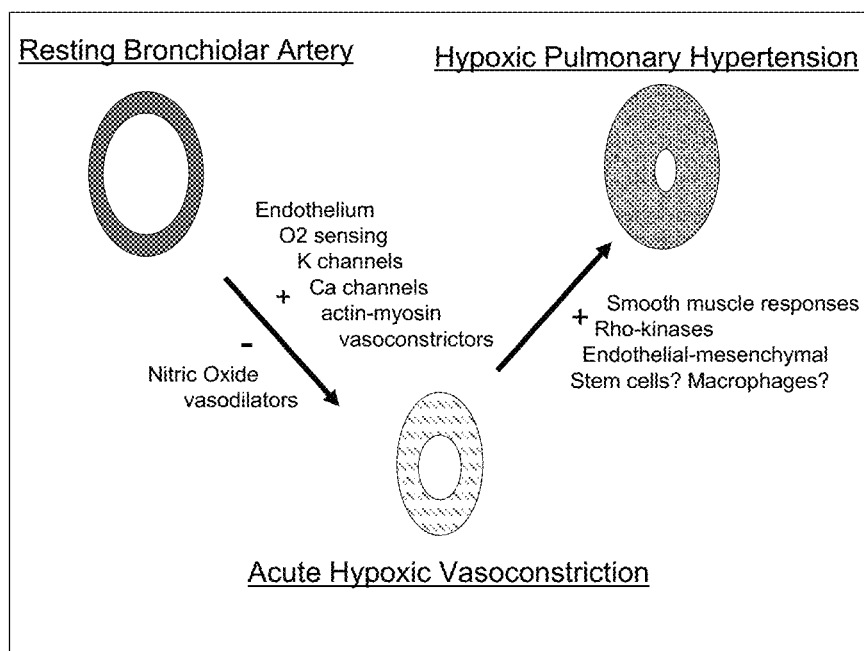
FIG. 2. Alveolar hypoxia leads to acute smooth muscle contraction in the small pulmonary arteries/arterioles. This is acute hypoxic vasoconstriction and raises the PA pressure. Chronic exposure to alveolar hypoxia leads to remodeling of the pulmonary circulation with thickening of the smooth muscle, and involvement of endothelium and other vessel components FIG. 3. Species differences in the acute hypoxic vasoconstriction response in the left panel and during chronic high altitude or hypoxic exposure in the right panel. *Bos Taurus* is a highly reactive animal acutely and has very high PA pressures chronically. It is not clear that the rise in PA pressure is linearly related to altitude as is drawn in the right hand panel.

Many signaling pathways are potential candidates (Rabinovitch, 2005). Relevant pathways include those involved in acute and chronic vasoconstriction, and those involved with remodeling of the arterial wall. Potential cells of interest include endothelium, smooth muscle, fibroblasts, mast cells, immune cells and all of the growth and apoptotic systems, as shown in FIG. 2. The list of known candidate mediators of interest is very large, and the actual gene of brisket disease may be as yet unidentified.

The genetic basis of variations in hypoxic pulmonary hypertension is poorly understood. Hypoxic vasoconstriction is the initial stimulus but does not fully control the final degree of pulmonary hypertension. There are likely to be multiple genes of effect, including growth genes, and it is likely that sets of polymorphisms will predispose to pulmonary hypertension during acute and chronic hypoxic exposure. In cattle there appears to be a major gene that determines the strength of hypoxic pulmonary hypertension.

Figure 3:
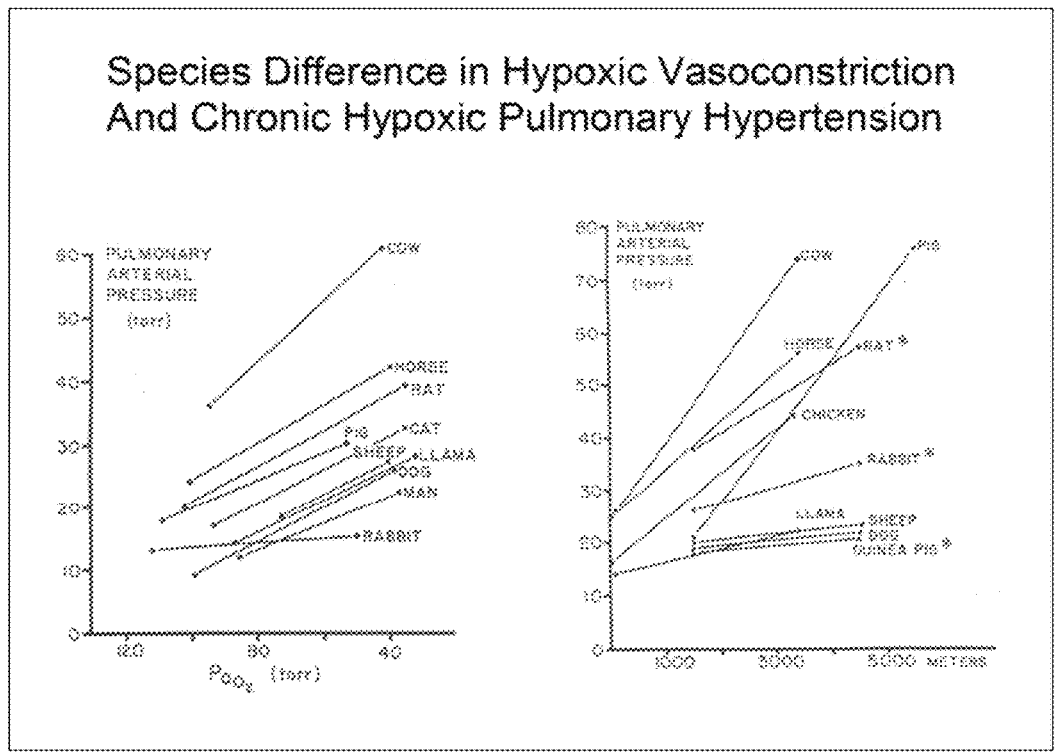

Brisket disease is the development of edema secondary to right heart failure in cattle that develop high altitude pulmonary hypertension (Heath and William, 1981, Grover, 1965, Rhodes, 2005, Grover, 2001, Glover and Newsom, 1915, Gjermundson, 2000 and Grover et al., 1963). The illness is called "brisket" disease because the edema occurs in the chest muscles (brisket), which are gravity dependent in cattle. Edema does not occur in the legs, presumably because of the tendon and tissue support and vasculature of the extremities. Brisket disease affects 5-10% of most, and 50% of some, herds moved to 8000 ft altitude (Weir et al., 1974). It was found in 6% of yearling deaths that occurred among feedlot cattle (Jensen et al., 1976). While brisket disease is found in many breeds taken to high altitude, most commonly Hereford and Angus, it is not present in all herds or animals, and some cattle can live at 7500-9000 feet above sea level without disease. The tendency to develop brisket disease is clearly inherited. Cattle with the pre-exposure tendency to hypoxic pulmonary hypertension pass the trait to their offspring, and cattle that thrive at altitude and do not develop brisket disease have resistant offspring (Grover, 1965 and Weir et al., 1974). The gene or genes controlling this phenotype are not known. Over 2 million head of cattle currently reside at risk at high altitude in the USA. Basal species differences in the pulmonary vascular response to acute and chronic hypoxia are well documented. Cattle and pigs have a high response, whereas sheep, llama and rabbits have a lesser response (Rhodes, 2005, Grover et al., 1963 and Will and Bisgard, 1975), as shown in FIG. 3.

It is not clear what predispositions determine the response. The innate degree of medial thickness of the pulmonary arteries roughly correlates with the severity of chronic pulmonary hypertension in most species (and in cattle), as does the basal hypoxic pressor response, and collateral ventilation may have a protective effect in situations of regional alveolar hypoxia (Grover et al., 1963, Will and Bisgard, 1975, Kuriyama and Wagner, 1981, Tucker et al., 1975, Hultgren and Grover, 1968 and Will et al., 1975). Chronic hypoxic pulmonary hypertension clearly involves the remodeling of the vascular bed, including changes in the intima, media and adventitia. Thus, genes involved in this condition contribute to the integrated vascular response to increased pressure rather than just to hypoxic vasoconstriction per se (Maggiorini and Leon-Velarde, 2003, Stenmark and McMurtry, 2005, Reeves, 2002, Das et al., 2002, Davie et al., 2004 and Short et al., 2004).

Figure 4:
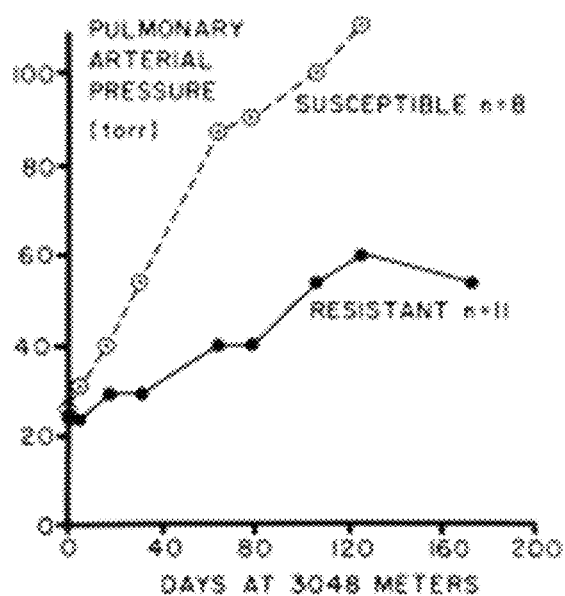
FIG. 4. Pulmonary arterial pressure as a function of time at altitude in offspring of either HAPH susceptible cattle or resistant cattle. The offspring of resistant cattle did not develop HAPH, but those descended from susceptible cattle had HAPH.
Figure 5:
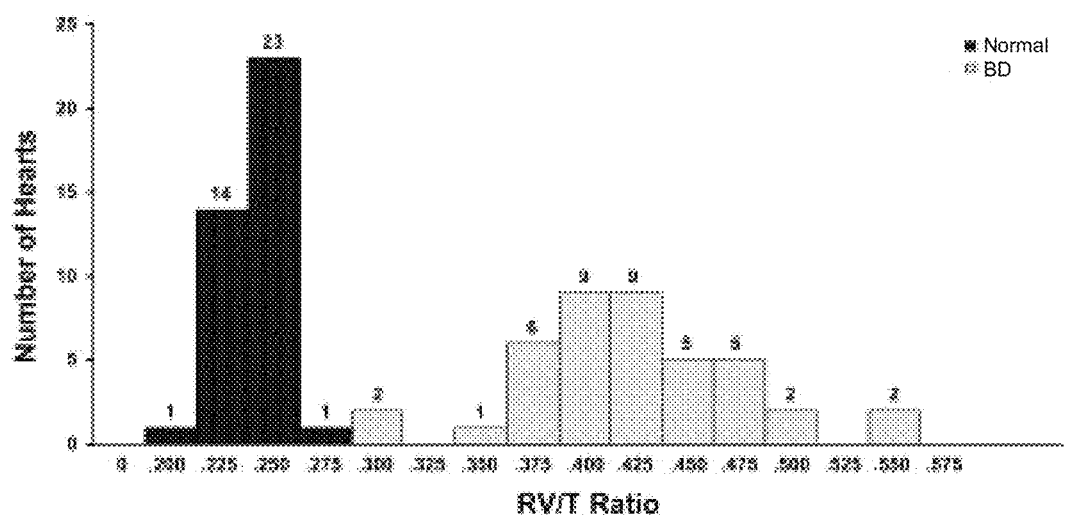
FIG. 5. Shows a bimodal distribution of right ventricular (RV) to total heart (H) weights taken from cattle residing at altitude. This bimodal distribution between normal and brisket disease cattle correlates with high altitude pulmonary hypertension (39) and suggests that there are two distinct variants, rather than a continuum of pressure response.

Evidence that HAPH in *Bos taurus* is an autosomal dominant trait is suggested by observations and breeding experiments (Heath and William, 1981, Rhodes, 2005, Weir et al., 1974, Droma et al., 2002, Hanaoka et al., 2003, Eddahibi et al., 2003, Rabinovitch, 2005 and 11,39, Grover, 2001). Brisket disease was first recognized as a risk in high altitude ranching in the early 1900's (Glover and Newsom, 1915). The rate of acquiring brisket disease in low altitude cattle brought to high altitude (10,000 ft) is about 10-50%. The prevalence among cattle chronically residing above 2100 m (about 7000 ft) has been reduced to only about one percent because of selective loss of susceptible cattle to heart failure or their removal from herds after PAH has been identified, but it is significantly higher (5-50%) among cattle who are recently moved from low altitude. To test the hypothesis that the susceptibility to brisket disease is heritable, Reeves and Grover bred a cohort of cattle with HAPH whose mean pulmonary arterial pressure (PA) was 50 mmHg and a group of resistant animals whose mean PA was 29 mmHg, all residing at 10,000 feet. In all experiments, PA pressure was directly measured by right heart catheterization (Weir et al., 1974). The 25 cattle were initially taken down to 4916 ft altitude where the cattle with HAPH recovered and then the cattle were bred within each group. Bulls and cows were equally represented. First generation offspring were studied at both low and high altitude. Mean PA pressures were 27+/−4 (SD) at low altitude. After residing at 10,000 feet for two months, the offspring of cattle with HAPH (brisket disease) had mean PA pressure of 87+/−7 (SE) and those from resistant stock had mean PA of 44 +/−3 mmHg Second generation breeding within these two cohorts of calves yielded the same pattern of susceptibility and resistance. Pressures continued to diverge over time at altitude. FIG. 4 shows the PA pressor response in offspring of susceptible and resistant cattle over time when returned to altitude (Grover et al., 1983).

Proof that the stimulus to pulmonary hypertension was hypoxia and not "altitude" was demonstrated by exposures in a hypoxic chamber at low altitude that showed similar pulmonary hypertensive responses. Arterial blood gas measurements in susceptible and resistant cattle revealed similar severity of hypoxemia, similar alveolar ventilation, (defined by the arterial carbon dioxide partial pressure, $PCO_2$), and only small differences in hematocrit, not sufficient to cause viscosity effects. In susceptible versus resistant cattle at altitude, $PO_2$ was 52 versus 50 (+/−6) mmHg, $PCO_2$ was 35 vs 37 (+/−7) mmHg, pH 7.4 in each group (+/−0.04) and hematocrit 43 vs 39 (+/−2). Finally, in order to test whether the pulmonary pressor response was specific to hypoxia, all cows were given intravenous prostaglandin F2 alpha, a potent pulmonary arterial pressor, and the response was the same (Grover et al., 1983). Darling and Holt also studied sire and calf pulmonary arterial pressure correlations in 1999 and concluded that brisket disease is caused by an autosomal dominant gene with variable expression (Darling and Holt, 1999).

Susceptibility to high altitude hypertension leading to brisket disease in cattle appears to be transmitted by an autosomal dominant gene with high penetrance that is affected by age and environment (altitude). The susceptibility is directly related to hypoxia and is not a consequence of hypoventilation, acidosis or secondary erythrocytosis. The illness can be recreated by hypoxic exposure at low altitude of susceptible animals. Animals that are biologically adapted to high altitude, such as the yak transmit their natural resistance to high altitude pulmonary hypertension when bred to cattle (Anand et al., 1986).

A. Assessing for the Presence of SNPs Using Genetic Methods

The methods described herein include determining the identity, e.g., the specific nucleotide, presence or absence, of a SNP associated with HAPH. Samples that are suitable for use in the methods described herein contain genetic material, e.g., genomic DNA (gDNA) or messenger RNA (mRNA). Such nucleic acids are may be extracted from biological samples such as blood, hair, semen (in the case of a bull), mucosal scrapings of the lining of the mouth, and may be extracted from other biological samples including urine or expectorant. The sample itself will typically include nucleated cells or tissue removed from the subject. The subject can be male or female, as well as an adult or young animal. In some embodiments, the sample can be obtained prenatally, either from a fetus or embryo or from the mother (e.g., from fetal or embryonic cells in the maternal circulation). Methods and reagents are known in the art for obtaining, processing, and analyzing samples.

In some cases, a biological sample may be processed for DNA or RNA isolation. For example, DNA or RNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al. (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include blood, hair, semen and tissue.

The presence or absence of the SNP can be determined using methods known in the art. For example, gel electrophoresis, capillary electrophoresis, size exclusion chromatography, sequencing, and/or arrays can be used to detect the presence or absence of specific response alleles. Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of an allele as described herein, i.e., by determining the identity of one or more alleles associated with a selected response. The identity of an allele can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

Other methods of nucleic acid analysis can include direct manual sequencing (Church and Gilbert, 1988; Sanger et al., 1977; U.S. Pat. No. 5,288,644); automated fluorescent sequencing; single-stranded conformation polymorphism assays (SSCP) (Schafer et al., 1995); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989); denaturing high performance liquid chromatography (DHPLC) (Underhill et al., 1997); infrared matrix-assisted laser desorption/ionization (IR-MALDI) mass spectrometry (WO 99/57318); mobility shift analysis (Orita et al., 1989); restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., *E. coli* mutS protein; allele-specific PCR, and combinations of such methods. See, e.g., U.S. Patent Publication No. 2004/0014095, which is incorporated herein by reference in its entirety.

Sequence analysis can also be used to detect specific polymorphic variants. For example, polymorphic variants can be detected by sequencing exons, introns, 5' untranslated sequences, or 3' untranslated sequences. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined. Real-time pyrophosphate DNA sequencing is yet another approach to detection of polymorphisms and polymorphic variants (Alderborn et al., 2000). Additional methods include, for example, PCR amplification in combination with denaturing high performance liquid chromatography (dHPLC) (Underhill et al., 1997).

PCR® refers to procedures in which target nucleic acid (e.g., genomic DNA) is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. See e.g., *PCR Primer: A Laboratory Manual*, Dieffenbach and Dveksler, (Eds.);

McPherson et al., 2000; Mattila et al., 1991; Eckert et al., 1991; PCR (eds. McPherson et al., IRL Press, Oxford); and U.S. Pat. No. 4,683,202. Other amplification methods that may be employed include the ligase chain reaction (LCR) (Wu and Wallace, 1989; Landegren et al., 1988), transcription amplification (Kwoh et al., 1989), self-sustained sequence replication (Guatelli et al., 1990), and nucleic acid based sequence amplification (NASBA). Guidelines for selecting primers for PCR amplification are well known in the art. See, e.g., McPherson et al. (2000). A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In some cases, PCR conditions and primers can be developed that amplify a product only when the variant allele is present or only when the wild type allele is present (MSPCR or allele-specific PCR). For example, patient DNA and a control can be amplified separately using either a wild-type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., 1994). The PNA probe can be designed to specifically hybridize to a nucleic acid comprising a polymorphic variant.

In some cases, allele-specific oligonucleotides can also be used to detect the presence of a polymorphic variant. For example, polymorphic variants can be detected by performing allele-specific hybridization or allele-specific restriction digests. Allele specific hybridization is an example of a method that can be used to detect sequence variants, including complete genotypes of a subject (e.g., a mammal such as a human). See Stoneking et al., 1991; Prince et al., 2001. An "allele-specific oligonucleotide" (also referred to herein as an "allele-specific oligonucleotide probe") is an oligonucleotide that is specific for particular a polymorphism can be prepared using standard methods (see, Ausubel et al., 2003). Allele-specific oligonucleotide probes typically can be approximately 10-50 base pairs, preferably approximately 15-30 base pairs, that specifically hybridizes to a nucleic acid region that contains a polymorphism. Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. In some cases, dot-blot hybridization of amplified oligonucleotides with allele-specific oligonucleotide (ASO) probes can be performed. See, for example, Saiki et al. (1986).

In some embodiments, allele-specific restriction digest analysis can be used to detect the existence of a polymorphic variant of a polymorphism, if alternate polymorphic variants of the polymorphism result in the creation or elimination of a restriction site. Allele-specific restriction digests can be performed in the following manner. A sample containing genomic DNA is obtained from the individual and genomic DNA is isolated for analysis. For nucleotide sequence variants that introduce a restriction site, restriction digest with the particular restriction enzyme can differentiate the alleles. In some cases, polymerase chain reaction (PCR) can be used to amplify a region comprising the polymorphic site, and restriction fragment length polymorphism analysis is conducted (see, Ausubel et al., 2003). The digestion pattern of the relevant DNA fragment indicates the presence or absence of a particular polymorphic variant of the polymorphism and is therefore indicative of the subject's response allele. For sequence variants that do not alter a common restriction site, mutagenic primers can be designed that introduce a restriction site when the variant allele is present or when the wild type allele is present. For example, a portion of a nucleic acid can be amplified using the mutagenic primer and a wild type primer, followed by digest with the appropriate restriction endonuclease.

In some embodiments, fluorescence polarization template-directed dye-terminator incorporation (FP-TDI) is used to determine which of multiple polymorphic variants of a polymorphism is present in a subject (Chen et al., 1999). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

In some cases, DNA containing an amplified portion may be dot-blotted, using standard methods (see Ausubel et al., 2003), and the blot contacted with the oligonucleotide probe. The presence of specific hybridization of the probe to the DNA is then detected. Specific hybridization of an allele-specific oligonucleotide probe (specific for a polymorphic variant indicative of a predicted response to a method of treating an SSD) to DNA from the subject is indicative of a subject's response allele.

The methods can include determining the genotype of a subject with respect to both copies of the polymorphic site present in the genome (i.e., both alleles). For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

Methods of nucleic acid analysis to detect polymorphisms and/or polymorphic variants can include, e.g., microarray analysis. Hybridization methods, such as Southern analysis, Northern analysis, or in situ hybridizations, can also be used (see, Ausubel et al., 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to the methods provided herein.

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70% (e.g., 80%, 90%, 95%, 98% or more) identity to the target sequence. The probe sequence must also be sufficiently long so that the probe exhibits selectivity for the target sequence over non-target sequences. For example, the probe will be at least 20 (e.g., 25, 30, 35, 50, 100, 200, 300, 400, 500, 600, 700, 800, 900 or more) nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

The probe can be a test probe such as a probe that can be used to detect polymorphisms in a region described herein (e.g., an allele associated with treatment response as described herein). In some embodiments, the probe can bind to another marker sequence associated with SZ, SPD, or SD as described herein or known in the art.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially such from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, (1998); Wheeless et al., (1994); U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), TEXAS RED™ (Molecular Probes, Inc., Eugene, Oreg.), 5-(and -6)-carboxy-X-rhodamine, lissamine rhodamine B, 5-(and -6)-carboxyfluorescein, fluorescein-5-isothiocyanate (FITC), 7-diethylaminocoumarin-3-carboxylic acid, tetramethylrhodamine-5-(and -6)-isothiocyanate, 5-(and -6)-carboxytetramethylrhodamine, 7-hydroxycoumarin-3-carboxylic acid, 6-[fluorescein 5-(and -6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and CASCADE™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

B. Markers in Linkage Disequilibrium (LD)

Linkage disequilibrium (LD) is a measure of the degree of association between alleles in a population. One of skill in the art will appreciate that alleles involving markers in LD with the polymorphisms described herein can also be used in a similar manner to those described herein. Methods of calculating LD are known in the art (see, e.g., Morton et al., 2001; Tapper et al., 2005; Maniatis et al., 2002). Thus, in some cases, the methods can include analysis of polymorphisms that are in LD with a polymorphism described herein. Methods are known in the art for identifying such polymorphisms; for example, the International HapMap Project provides a public database that can be used, see hapmap.org, as well as The International HapMap Consortium (2003) and The International HapMap Consortium (2005). Generally, it will be desirable to use a HapMap constructed using data from individuals who share ethnicity with the subject. For example, a HapMap for Caucasians would ideally be used to identify markers in LD with an exemplary marker described herein for use in genotyping a subject of Caucasian descent.

Alternatively, methods described herein can include analysis of polymorphisms that show a correlation coefficient ($r^2$) of value >0.5 with the markers described herein. Results can be obtained from on line public resources such as HapMap.org on the World Wide Web. The correlation coefficient is a measure of LD, and reflects the degree to which alleles at two loci (for example, two SNPs) occur together, such that an allele at one SNP position can predict the correlated allele at a second SNP position, in the case where $r^2$ is >0.5.

C. Protein Based Methods

1. Immunoassays

Thus, in accordance with the present invention, methods are provided for the assaying of protein expression in patients suffering from gliomas. As discussed above, the principle applications of this assay are to: (a) determine what grade of glioma a given patient suffers from; and (b) determine the likelihood and extent of patient survival. In each of these assays, the expression of a particular set of target proteins, set forth in the preceding sections, will be measured.

There are a variety of methods that can be used to assess protein expression. One such approach is to perform protein identification with the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab').sub.2, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (see, e.g., Antibodies: A Laboratory Manual, Cold Spring Harbor Laboratory, 1988; incorporated herein by reference). In particular, antibodies to calcyclin, calpactin I light chain, astrocytic phosphoprotein PEA-15 and tubulin-specific chaperone A are contemplated.

In accordance with the present invention, immunodetection methods are provided. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle & Ben-Zeev O, 1999; Gulbis & Galand, 1993; De Jager et al., 1993; and Nakamura et al., 1987; each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

2. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that are useful for grading gliomas and predicting glioma patient survival, without regard for the identity of specific proteins. Alternatively, given the established links with calcyclin, calpactin I light chain, astrocytic phosphoprotein PEA-15 and tubulin-specific chaperone A, mass spectrometry may be used to look for the levels of these proteins particularly.

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 .mu.L/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10.\mathrm{sup}.6$ to $10.\mathrm{sup}.7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757, 994; RE 35,413; and 5,986,258.

In ESI tandem mass spectroscopy (ESI/S/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

Secondary ion mass spectroscopy, or SIMS, is an analytical method that uses ionized particles emitted from a surface for mass spectroscopy at a sensitivity of detection of a few parts per billion. The sample, surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

D. Application of Results

Described herein are a variety of methods for predicting cattle's susceptibility to HAPH based on the presence or absence of an allele defined by the SNPs designated 28662654 and 28662666 on bovine chromosome 11 at exon 12 of the EPAS1 gene. As used herein, "determining the identity of an allele" includes obtaining information regarding the identity (i.e., of a specific nucleotide), presence or absence of one or more specific SNP alleles in a subject. Determining the identity of an allele can, but need not, include obtaining a sample comprising DNA or protein from a subject, and/or assessing the identity, presence or absence of one or more markers in the sample. The individual or organization who determines the identity of the allele need not actually carry out the physical analysis of a sample from a subject; the methods can include using information obtained by analysis of the sample by a third party. Thus, the methods can include steps that occur at more than one site. For example, a sample can be obtained from a subject at a first site, such as at a ranch or breeding facility. The sample can be analyzed at the same or a second site, e.g., at a laboratory or other testing facility.

Determining the identity of an allele can also include or consist of reviewing a subject's medical history, where the medical history includes information regarding the identity, presence or absence of one or more response alleles in the subject, e.g., results of a genetic test.

In some embodiments, to determine the identity of an allele described herein, a biological sample that includes nucleated cells (such as blood, hair, semen, a cheek swab or mouthwash) is prepared and analyzed for the presence or absence of preselected markers. Such diagnoses may be performed by diagnostic laboratories, or, alternatively, diagnostic kits can be manufactured and sold to ranchers or breeders. Diagnostic or prognostic tests can be performed as described herein or using well known techniques, such as described in U.S. Pat. No. 5,800,998.

Results of these tests, and optionally interpretive information, can be returned to the subject, a buyer, a breeder or other a third party. The results can be used in a number of ways. The information can be, e.g., communicated to the owner or potential buyer of the tested subject, e.g., with a prognosis and optionally interpretive materials that help the owner or potential buyer understand the test results and prognosis. The information can be used to determine whether to buy or breed the animal, or to transport it to or from a high altitude environment. The information may also simply indicated whether an animal should be assigned to a specific category, e.g., a category associated with HAPH or risk thereof. The presence or absence of the response allele in a patient may be ascertained by using any of the methods described herein.

III. CATTLE BREEDS

The methods described herein may be applied against all *Bos taurus* and *Bos primigenius* breeds as no breeds are appear unaffected by HAPH. In North America, breeds commonly affected are black angus, Hereford, red angus, simmental, limousine, balancer, stabilizer, south Devon, galloway, black irish and all known miniature breeds of cattle.

IV. EPAS1 AND HIF-2α

Endothelial PAS domain-containing protein 1 (also known as Hypoxia-inducible factor-2α (HIF-2α)) is a protein that in humans is encoded by the EPAS1 gene. This gene encodes a half of a transcription factor involved in the induction of genes regulated by oxygen, which is induced as oxygen levels fall (hypoxia). The encoded protein contains a basic helix-loop-helix domain protein dimerization domain as well as a domain found in proteins in signal transduction pathways which respond to oxygen levels. EPAS1 is involved in the development of the embryonic heart and is expressed in the endothelial cells that line the walls of the blood vessels in the umbilical cord. It is essential in maintaining catecholamine homeostasis and protection against heart failure during early embryonic development.

Catecholamines include epinephrine and norepinephrine. It is important for the production of catecholamines to remain in homeostatic conditions so that both the delicate fetal heart and the adult heart do not overexert themselves and induce heart failure. Catecholamine production in the embryo is related to control of cardiac output by increasing the fetal heart rate. Mutations in this gene are associated with erythrocytosis familial type 4 pulmonary hypertension and chronic mountain sickness. There is also evidence that certain variants of this gene provide protection for people living at high altitude. EPAS1 is useful in high altitudes as a short term adaptive response. However, EPAS1 can also cause excessive production of red blood cells leading to chronic mountain sickness that can lead to death and inhibited reproductive abilities. Some mutations that increase its expression are associated with increased hypertension and stroke at low altitude, with symptoms similar to mountain sickness. People permanently living at high altitudes might experience selection of EPAS1 to reduce the fitness consequences of excessive red blood cell production.

HIF-2α abundance (and its subsequent activity) is regulated transcriptionally in an NF-κB-dependent manner. In addition, the coordinated activity of the prolyl hydroxylases (PHDs) maintains the appropriate balance of HIF-2α protein in the post-translation phase. PHDs rely on iron among other molecules to hydroxylate HIF-1 and HIF-2α; as such, iron chelators such as DFO have proven successful in HIF-1alpha stabilization. HBO (hyperbaric oxygen therapy) and HIF-1α imitators such as cobalt chloride have also been successfully utilized. Hypoxia is the environmental stimulus that reduces hydroxylation of HIF-2α and allows it to initiate multiple transcription events.

V. ARTICLES OF MANUFACTURE

Also provided herein are articles of manufacture comprising probes that hybridize to or prime near the region of chromosome containing the SNP described herein. For example, any of the probes for detecting the SNP described herein can be combined with packaging material to generate articles of manufacture or kits. The kit can include one or more other elements including: instructions for use; and other reagents such as a label or an agent useful for attaching a label to the probe. Instructions for use can include instructions for a method described herein. Other instructions can include instructions for attaching a label to the probe, instructions for performing analysis with the probe, and/or instructions for obtaining a sample to be analyzed from a subject. In some cases, the kit can include a labeled probe that hybridizes to a region of human chromosome as described herein.

The kit can also include one or more additional reference or control probes that hybridize to the same chromosome or another chromosome or portion thereof. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes. Kits for use in self-testing can also be provided. Such test kits can include devices and instructions that a subject can use to obtain a biological sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

VI. DATABASES AND REPORTS

Also provided herein are databases that include medical information including the genetic make up of a subject. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular allele or genotype and the information regarding the subject.

The methods described herein can also include the generation of reports, e.g., for use by a subject, care giver, payor, or researcher, that include information regarding a subject's response allele(s), and optionally further information such as treatments administered, treatment history, medical history, predicted response, and actual response. The reports can be recorded in a tangible medium, e.g., a computer-readable disk, a solid state memory device, or an optical storage device.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

From a herd of 41 cattle residing at high altitude >7000 feet, the inventors studied 5 most affected, mean PA 94 mmHg and 5 unaffected, mean PA 31. To ensure that the cattle were most distantly related, the inventors genotyped 10 microsatellite markers, calculated pairwise "distance" score as the number of alleles that differ between samples and selected the 5 most distantly related cattle in each group. WES was done using Illumina HiSeq 2500. Sequences were aligned to the cow genome bosTau6 (UMD3.1) using BWA. SNPs within 10 bases from an insertion/deletion site were removed, as were genotypes with GQ<30. The variant calls were annotated using ANNOVAR. The inventors analyzed data using an autosomal dominant model with a cutoff that required that at least 4 of 5 control samples would be homozygous negative for a variant and at least 4 of 5 of the affected heterozygous for a variant. Of 102 SNPs, they selected 6 based on their screening signal and potential function on the HAPH. Sequence variants were confirmed by Sanger sequencing. The remaining 31/41 were genotyped by Taqman assay. The inventors also tested a small lowland herd for the variant frequency.

Results

High altitude pulmonary hypertension (HAPH) in cattle has heritable features that appear to be autosomal dominant. The genetic associations with this response to hypoxia are unknown. The trait has no known phenotype except at altitude so carriage may be common in lowland cattle. The inventors sought to discover candidates with whole exome sequencing (WES). Two variants in exon 12 of the EPAS1 gene in a cis haplotype (bovine chromosome 11 position 28662654 and 28662666) appear to associate with HAHP (p<0.00005 by Fisher's exact test). In the herd, 14 of 20 (70%) with mean PA pressure 52-109 mmHg and 3 of 21 (14%) with PA of 29-38 had the variants. 12 of 32 (37%) of cattle from a lowland herd carry the variants.

Discussion

Two variants in haplotype are enriched in the EPAS1 gene in cattle with HAPH compared to unaffected low pressure cattle at high altitude. This data suggests that EPAS1 is a candidate gene for bovine HAPH. Studies are needed to determine if this variant causes a gain of function of HIF-2α. It is not known if this variant occurs in humans with PH related to hypoxia.

Example 2

Methods

Collection of Samples and Measurement of PAP
The inventors obtained blood from Black Angus cattle of both genders from 4 sites, aged 12-18 months, residing at 5200-7850 feet, by jugular vein puncture on the same day of right heart catheterization, done to screen for HAPH, and blood from an Alabama herd of cattle residing near sea level. The project was approved by the Vanderbilt Medical Center IACUC.
DNA Isolation and Microsatellite-Based Genotyping
DNA was isolated from whole blood using QIAmp DNA mini-kit as directed by the manufacturer's instructions (Qiagen, Valencia, Calif., USA) and subsequently quantified using a spectrophotometer. Samples were genotyped using the StockMarks for Cattle Bovine Genotyping kit (Cat. Number 4307480) (Life Technologies, Grand Island, N.Y., USA).

Whole Exome Sequencing (WES) and Data Preprocessing
The inventors used Agilent SureSelect XT Bovine All Exon kit (Cat. Number 5190-5448; Santa Clara Calif., USA) to capture the cow exome. The captured DNA library was then sequenced on an Illumina HiSeq2000 instrument. The sequences were aligned to the cow genome bosTau6 (UMD3.1) using Burrows-Wheeler Aligner (BWA) (bio-bwa.sourceforge.net). Duplicates were marked using Picard, and the sequences were locally realigned and base quality score was recalibrated using the Genome Analysis Tool Kit (GATK) (world-wide-web at broadinstitute.org/gatk/). Joint genotype calling was performed using GATK, followed by "hard filtering" as recommended on the GATK website. In addition, variations within 10 bases from an insertion/deletion site were removed, and genotypes with GQ<30 were removed. The variant calls were annotated using ANNOVAR (world-wide-web at openbioinformatics.org/annovar/).
Sanger Sequencing and Taqman Analysis
All DNA sequencing was carried out using BigDye (Life Technologies, Carlsbad, Calif.) according to manufacturers instructions. Taqman assays were obtained from Life Technologies (Carlsbad, Calif., USA). The assays targeted the variations found on WES and were designed so that the wild type allele utilized the VIC probe and the minor allele utilized the FAM probe. Analysis was done on 5 ng of genomic DNA using ABI PRISM 7500 instrument (Life Technologies Carlsbad, Calif., LISA) per the manufacturer's instructions.
Protein Stability Analysis
The two EPAS1 variants A606T and G610S were individually submitted to the MuPro website (word-wide-web at ics.uci.edu/~baldig/mutation/html) in conjunction with the Bovine EPAS1 protein sequence (NP_777150) to determine their impact on protein stability. To determine the effect of each amino acid substitution on protein function they were submitted to the SIFT (world-wide-web at sift.jcvi.org/wwwSIFT seq submit2.html) and Polyphen-2 (world-wide-web at genetics.bwh.harvard.edu.pph2/) for analysis.
Gene Expression Array Analysis
Of 171 genes upregulated by hypoxia in the Broad Institute set Elvidge_Hypoxia_Up (Elvidge et al., 2006), 68 have expression values above 7 as a maximum in either affected or unaffected data sets (thus, above the noise). Of these 68, 26 are upregulated in the affected group compared to the unaffected (p<0.05 by uncorrected t-test, fc>1.25) (Table 3; p<0.0001), or 38%, while 1 is downregulated (1.5%). Based on the total numbers of up or down regulated in genes expressed above the noise in the overall data set using the same criteria, the inventors' expectation values are 7% upregulated and 8% downregulated (or 5 genes upregulated and 5 genes downregulated). Chi squared is thus 96.4 with 2 degrees of freedom, for a 2-tailed p value of less than 0.0001, Table 3.

Results

Using whole exome sequencing (WES) and an autosomal dominant model in 5 extreme HAPH and 5 unaffected cattle living at high altitude, the inventors found two variants, in cis, in exon 12 of the Endothelial PAS domain-containing protein 1 (EPAS1) gene that encodes a hypoxia inducible factor, HIF2α. They tested these results in 31 additional animals. The variants were present in 75% of the 20 cattle with mean pulmonary arterial pressure (PAP)>50 mmHg, in all 5 cattle with extreme HAPH (PAP>94 mmHg), and in 19% of 21 unaffected with PAP<39 mmHg. The inventors replicated the finding in a second, unrelated herd from Wyoming in which 11 of 15 HAPH and only 3 of 16 unaffected were carriers. They also found higher mRNA expression in variant carriers than unaffected in 26 of 27 genes known to be targets of HIF2α. This double variant haplotype in EPAS1 is likely a gain-of-function mutation that requires a gene-environment interaction for expression.

Bos taurus has one of the highest acute and chronic hypoxic PAP responses of all species (Rhodes, 2005, Grover et al., 1965 and Grover, 1965). Cattle have a basal sea level mean PAP of approximately 27-29 mmHg, versus only 14 mmHg in human. There is no strict definition of pulmonary hypertension in cattle, but at age greater than 12 months and residence at or above 7000 feet altitude, a mean PAP of 31-41 mmHg is considered normal, and above 49 mmHg is considered at high risk for brisket disease (Berge et al., In: Proc. 10$^{th}$ World Congr. Appl. Livestock Prod. 2014., sas.org/docs/default-source/wcgalp-posters/ 430_paper_9946_manuscript_1110_0.pdf?sfvrsn=2, 2014 and Gjermundson, 2000). PAPs between 42 and 48 mm Hg are in a gray zone. PAP rises with duration at high altitude, the degree of altitude, and age of the animal. Some animals develop HAPH at altitudes near 5000 ft.

Brisket disease was first recognized in high altitude ranching in the early 1900's (Glover and Newsom, 1915 and Grover, 2001). Evidence that HAPH in cattle is an autosomal dominant trait was suggested by breeding experiments by Grover and Reeves (Grover et al., 1965a, Grover, 1965b, Weir et al., 1974 and Will et al., 1975). A few studies have investigated the genetic basis of HAPH but no genes with a high likely impact have been identified (Newman et al., 2011 and Cockrum et al., 2014). Epidemiological studies in high altitude cattle have found influences of age, gender, birth weight and growth rate in addition to heritability, and that early death in high altitude calves is associated with undiagnosed pulmonary hypertension (Shirley et al., 2008 and Neary et al., 2013).

HAPH affects 5-10% of most, and up to 50% of some herds moved from low altitude to >7000 ft altitude ranches (Holt and Callan, 2007, Weir et al., 1974 and Gjermundson, 2000). Affected cattle may die of right heart failure if not identified and moved to lower altitude. Over 2 million head of cattle reside at high altitude in the USA and the annual losses to ranchers are estimated at 3 million dollars a year (Holt and Callan, 2007 and Gjermundson, 2000). There is no known measurement at low altitude to predict which cattle will develop HAPH upon ascent. The high rate of development of HAPH in cattle shipped to high altitude suggested to us that the variant was common in lowland herds. Human HAPH is a worldwide problem, with over 140 million high altitude dwellers at risk (Penaloza and Arias-Stella, 2007 and Pasha and Newman, 2010).

Figure 6:
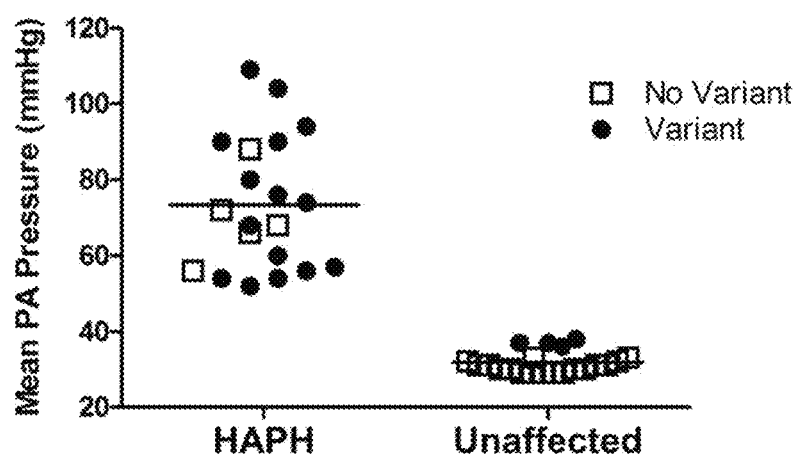
FIG. 6. Mean pulmonary arterial pressure in two groups of cattle dwelling at high altitude. Of the 20 HAPH (high altitude pulmonary hypertension PAP>50 mmHg), 15 carried the EPAS1 variant and all of the cattle with the highest PAP carried the variant. Four of the 21 unaffected cattle carried the variant, and these 4 had the highest pressure, albeit normal PAP<38 mmHg of the group.

The inventors sampled 41 (30 bulls and 11 cows) cattle residing at high altitude from three ranches at altitudes of 4850, 7200 and 8590 ft. All cattle underwent right heart catheterization by an experienced veterinarian (TNH) at rest to measure PAP and draw blood for DNA testing. Twenty cattle had HAPH (PAP>50 mmHg) and 21 had PAP<39 mmHg. The inventors used comparative WES analysis of DNA from cattle with HAPH versus unaffected controls to seek any important variant. To ensure the selected cattle were as genetically diverse as possible, the inventors genotyped 10 microsatellite markers on all DNA samples and calculated pairwise "distance" score as the number of alleles that differed between samples, using SimpleSeq2. The 5 cattle with the highest diversity in the high PAP group had mean PAP of 94.2+/−5.3 and the 5 cattle with the highest diversity in the low PAP group (unaffected) had mean PAP of 30.8 +/−0.8. (FIG. 6). The inventors generated an average of 10 Gb of sequence per animal as paired-end 100 bp reads by WES at around 80-fold coverage. About 97% of the target regions had sufficient coverage to pass the inventors' thresholds for variant calling. Due to small initial sample size, they focused only on non-synonymous variants, and short coding insertions or deletions.

Figure 7:
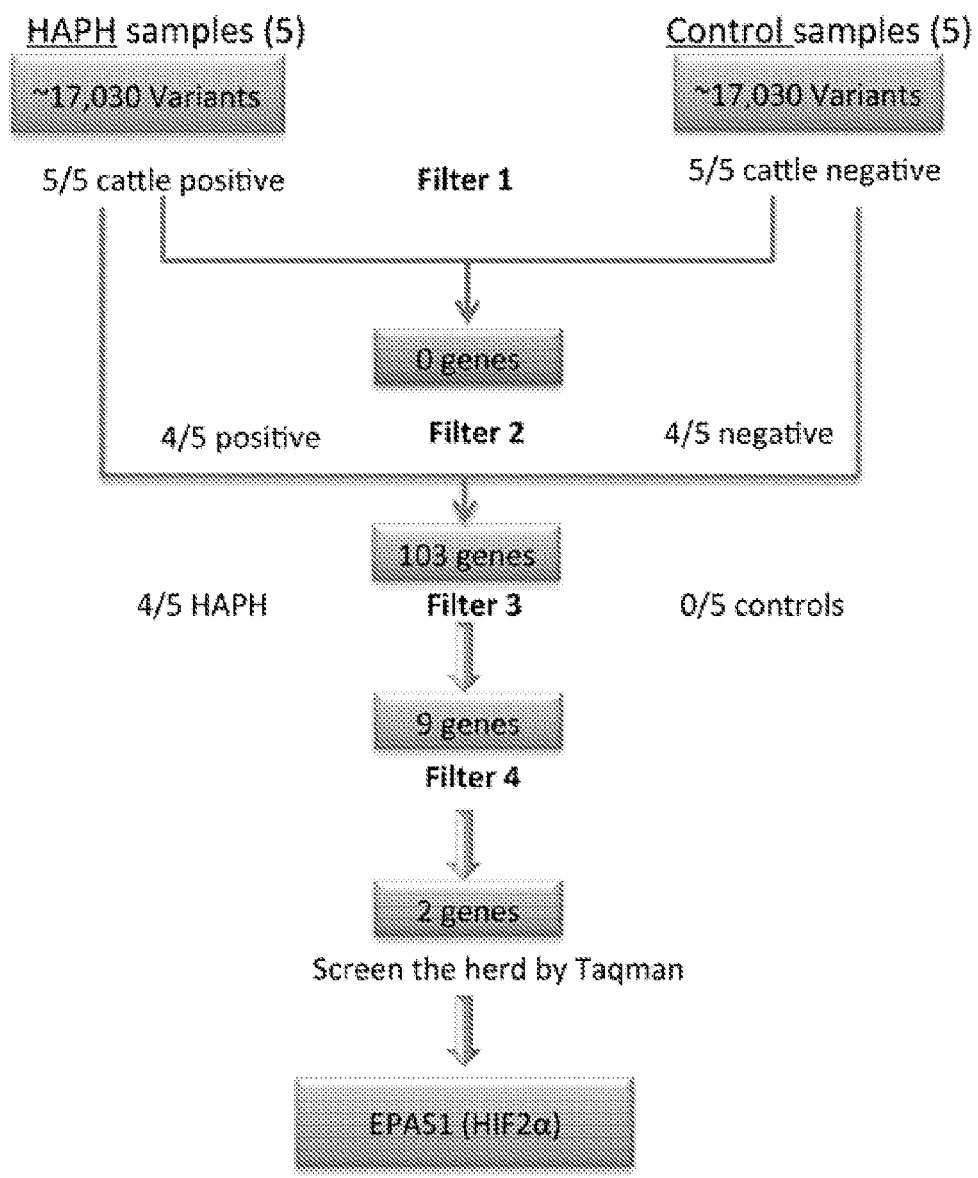
FIG. 7. Sequence of filtering and analysis of WES data using the autosomal dominant model. First filter was no variant found in all five HAPH and none unaffected. Second filter was presence in 4/5 HAPH and 1/5 affected yielding 102 genes. Filter 3 was 4/5 HAPH and 0/5 unaffectered, yielding 9 genes. Sanger sequencing reduced the number to two candidates, EPAS1 and PDPR. Taqman assay revealed no association with PDPR, but highly significant association of HAPH with EPAS1 variant.

The inventors used an autosomal dominant model for screening, (FIG. 7). They used a simple algorithm that at least 4 of the 5 affected samples carry the same variant and 4 of the 5 unaffected samples be homozygous negative and for the variant. This generated a list of 103 genes with a sequence variation (Table 2) of which nine genes (Table 1) were found to be homozygous negative in all unaffected and heterozygous positive for a variant in 4/5 of affected. These 9 genes included EPAS1 which contained two variants in close proximity to each other, c.1816G-A and c.1828G-A, both in exon 12. Each sample had either both variants or none, indicating that both were on the same haplotype. Sanger sequencing of 10 additional samples, 5 affected and 5 unaffected, narrowed the list to two genes, EPAS1 and pyruvate dehydrogenase phosphatase regulatory subunit (PDPR) in which none of the 10 unaffected and 8 of the 10 affected samples had the variant. The EPAS1 variants predicted two non-synonymous substitutions, p.A606T and p.G610S, in the oxygen dependent degradation domain of the HIF2α protein.

The inventors then designed Taqman assays for the two EPAS1 variants and the one PDPR variant and genotyped 10 additional HAPH cattle and 11 additional unaffected animals. Of these, 7 cases and 4 affected had the EPAS1 variants, and every carrier had both variants. The 4 unaffected cattle that carried the variant had the highest PAPs among all 21 unaffected (36-38 mmHg), at the upper limit of normal. Taking all 41 cattle, 15 of the 20 samples with PAP>50 mmHg were positive for the two EPAS1 variants and 4 of 21 with PAP<39 mmHg had the variants, with a chi square p-value of $3.3 \times 10^{-6}$. Wilcoxon's rank sum tests on PAP between EPAS1 variant carriers and non-carriers was also significant, $p=4.6 \times 10^{-5}$. PDPR variant did not segregate with high PAP; 10 of the 20 affected samples and 5 of the 21 unaffected had the PDPR variant (p<0.08). With a likelihood of development of HAPH at 50%, the positive predictive value of the EPAS1 variants would be 79.7% and the negative predictive value would be 76.4%. The relative risk for HAPH between a carrier and a non-carrier is estimated to be 3.47 (1.55-7.77), and the odds ratio is estimated as 12.75 (2.9-66.4). The inventors found no variants that segregated with HAPH in a number of known PH genes, include those encoding BMPR2, ACVRL1, Cav1, VHL and endogolin The inventors tested and replicated the variant data in a second herd, residing at 7100 ft in Wyoming. These were young cattle, studied about 6 months of age, but they had been born and raised at this altitude. Eleven of the 15 cattle with PAP≥45 mmHg, but only 3 of 16 with PAP≤39 carried the variant, chi square p-value<0.0023, Table 2.

Because of the high rate of development of HAPH in lowland cattle moving to high altitude, the inventors predicted that the variants would be present at a reasonably high frequency in lowland cattle. To test this hypothesis, they obtained DNA samples from 32 cattle residing in Alabama, USA to screen for the two EPAS1 variants. Thirteen of the 32 samples had the two variants (41%), with every positive sample carrying both variants.

Because the two variants introduce non-synonymous changes to the HIF2α protein, the inventors investigated if the corresponding residues are conserved among species. As shown (FIG. 9), a comparison of number of mammalian EPAS1 protein sequence showed that these two amino acids are somewhat conserved. Interestingly, yak which has a nearly identical EPAS1 protein sequence to cow, and has adapted to high altitude, does not have either of these changes, while sheep are known to have one of the two SNPs, at codon 606, but not the second. Sheep do not suffer from high altitude disease but given that all affected cows have both the variation it may suggest both changes need to be present together to alter function of the protein in a significant fashion the other possibility could be that in sheep the HIF pathway is configured in a way that it can tolerate one variant change.

Mutations in the same oxygen dependent domain in the human EPAS1 gene show increased stability and decreased degradation associated with increased downstream transcriptional activity, consistent with a gain of function (Pasha and Newman, 2010). The inventors used computational tools to predict the function of the variants residues in cattle. The analysis showed that each variant was predicted to significantly increase the protein stability of HIF2α. Two stabilizing variants together in cis are predicted to result in an even more stable protein. The inventors note that the two residues were in perfect linkage disequilibrium in their data.

Since these variants were predicted to increase HIF2α stability, to inventors hypothesized that this would result in upregulation of downstream HIF2α target genes. They thus looked at differential expression between peripheral blood mononuclear cells from cattle with HPAH and HIF2α variants and unaffected cattle without HIF2α variant by analyzing their previously published gene expression array data (Newman et al., 2011). They found that in cattle containing the double HIF2α variant, transcription of HIF target genes was significantly overrepresented (p<0.0001 by chi-square test), with 26 of 27 HIF target genes significantly upregulated compared to unaffected cattle, Table 3 (p<0.0001).

Human EPAS1 and HIF1α a are basic helix-loop-helix transcription factors that contain a Per Arnt Sim (PAS) domain and share 48% sequence homology (Semenza, 2012 and Shimoda and Semenza, 2011). During sufficient oxygen availability, the resulting HIF proteins are constantly degraded, but are released for function during cell or tissue hypoxia. Under hypoxic conditions HIFs are protected by inhibition of oxygen-dependent hydroxylation of specific residues in the oxygen-dependent degradation domain. This prevents interaction with the Von Hippel Lindau ubiquitin ligase complex and proteasomal destruction. HIF2α is found in all human tissues including lung and lung vasculature. The downstream effects of HIF2α include regulation of angiogenic factors including VEGF and TGF-α, and cell permeability and stimulation of erythropoietic and glycolytic proteins (Semenza, 2012, Shimoda and Semenza, 2011 and Hickey and Simon, 2006).

Germline EPAS1 gain-of-function rare variants can cause familial erythrocytosis and/or pulmonary hypertension (Gale et al., 2008 and Percy et al., 2008). A von Hippel-Lindau mutation that reduces destruction of HIF2α is found in Chuvash populations and is associated with modest pulmonary hypertension and erythrocytosis (Hickey et al., 2010). Transgenic mice carrying a G536W variant in EPAS1 developed high right ventricular systolic pressure and medial hypertrophy of pulmonary arteries in addition to erythrocytosis under normoxic conditions (Tan et al., 2013). Thus, HIF2α dysregulation is well recognized in association with pulmonary hypertension, frequently in context of erythrocytosis, with or without severe hypoxemia.

In contrast, probable loss of function variants in EGLN1 and HIF2α were found to be enriched in residents of the Tibetan Plateau (Beall et al., 2010, Xin et al., 2010 and Simonson et al., 2010). Native Tibetans are recognized to have beneficial adaptation to high altitude, with less polycythemia, less hemoglobin desaturation, preserved ventilatory responses and normal birth weights. The inference from these studies is that loss of function of HIF2α driven either directly or indirectly by down regulation of modifying proteins may be beneficial in states of chronic hypoxia where chronic HIF protein stabilization may be detrimental.

CONCLUSION

In summary, the inventors found that two cis variants in EPAS1 (HIF2α) are highly associated with HAPH in cattle residing at high altitude in the Rocky Mountains, USA. Given what is known about HIF2α function, these data suggest that EPAS1 is likely a major gene for HPAH in cattle. Additional studies are needed to clarify its biological role in HAPH in cattle and any role of the variant in human HAPH.

TABLE 1

Top 9 candidate genes of 102 based on initial filter of prevalence in 4 of 5 affected and 1 of 5 unaffected cattle

| Gene | Symbol | Function | Cow chromosome | Ref Seq mRNA | Non Synonymous Variation | Location (Btau_4.6.1) |
|---|---|---|---|---|---|---|
| Budding Uninhibited by Benzimidazoles 1 | BUB1 | Mitotic spindle checkpoint kinase. | 11 | NM_001102011 | Exon10: c.G1165A: p.V389M | 1571369 |
| Complement Component 4A | C4A | Complement factor 4, part of the classical activation pathway. | 23 | NM_001166485 | Exon11: c.A1262G: p.Q421R | 27193512 |
| Feline Leukemia Virus Subgroup C Cellular Receptor 2 | FLVCR2 | Calcium transporter. | 10 | NM_001192143 | Exon9: c.C1239G: p.D413E | 87200257 |

TABLE 1-continued

Top 9 candidate genes of 102 based on initial filter of prevalence in 4 of 5 affected and 1 of 5 unaffected cattle

| Gene | Symbol | Function | Cow chromosome | Ref Seq mRNA | Non Synonymous Variation | Location (Btau_4.6.1) |
|---|---|---|---|---|---|---|
| Leucine-Rich Repeat-Containing Protein 17 | LRRC17 | A negative regulator of receptor activator of NF-κB ligand. | 4 | NM_001078150 | Exon2: c.A95T: p.H32L | 44501073 |
| Pyruvate Dehydrogenase Phosphatase Regulatory Subunit | PDPR | Pyruvate metabolism and Respiratory electron transport. | 18 | NM_174781 | Exon3: c.C327G: p.H109Q | 1939296 |
| Regulator Of G-Protein Signaling 18 | RGS18 | Regulator of G-protein signaling family. | 16 | NM_001192971 | Exon4: c.C397T: p.R133C | 13749384 |
| Zinc Finger MYM-Type Protein 6 | ZMYM6 | Regulation of cell morphology and cytoskeletal organization. | 3 | NM_001206292 | Exon16: c.G2834C: p.C945S | 111275016 |
| Endothelial PAS Domain-Containing Protein 1 (also known as Hypoxia-Inducible Factor 2-α) | EPAS1 | A transcription factor involved in the induction of genes regulated by oxygen. | 11 | NM_174725 | Exon12: c.G1816A: p.A606T | 28662654 |
| Rho GTPase Activating Protein 20 | ARHGAP20 | GTPase activator for the Rho-type GTPases by converting them to an inactive GDP-bound state. | 15 | NM_001206733 | Exon15: c.C3262T: p.P1088S | 20909547 |

TABLE 2

Mean pulmonary artery pressure (PAP) in 31 cattle residing at 7100 ft in Wyoming

| Ear Tag # | mPAP (mmHg) | Zygosity |
|---|---|---|
| 2155 | 64 | Heterozyote G/A |
| 2355 | 54 | Heterozygote G/A |
| 2171 | 53 | Heterozygote G/A |
| 2201 | 53 | Heterozygote G/A |
| 2156 | 48 | Wild-type G/G |
| 2200 | 48 | Homozygote A/A |
| 2221 | 48 | Heterozygote G/A |
| 2033 | 47 | Wild-type G/G |
| 2064 | 47 | Heterozygote G/A |
| 2213 | 47 | Heterozygote G/A |
| 2158 | 45 | Homozygote A/A |
| 2204 | 45 | Wild-type G/G |
| 2229 | 45 | Homozygote A/A |
| 2231 | 45 | Heterozygote G/A |
| 2337 | 45 | Wild-type G/G |
| mPAP below this line ≤39 | | |
| 2052 | 39 | Wild-type G/G |
| 2135 | 39 | Homozygote A/A |
| 2181 | 39 | Heterozygote G/A |
| 2311 | 39 | Wild-type G/G |
| 2409 | 39 | Wild-type GlG |
| 2019 | 38 | Wild-type GlG |
| 2035 | 38 | Wild-type GlG |
| 2039 | 38 | Wild-type GlG |
| 2290 | 38 | Wild-type GlG |
| 2356 | 38 | Wild-type GlG |

TABLE 2-continued

Mean pulmonary artery pressure (PAP) in 31 cattle residing at 7100 ft in Wyoming

| Ear Tag # | mPAP (mmHg) | Zygosity |
|---|---|---|
| 2111 | 37 | Wild-type G/G |
| 2248 | 37 | Wild-type GIG |
| 2396 | 37 | Homozygote A/A |
| 2349 | 36 | Wild-type GIG |
| 2402 | 36 | Wild-type GIG |
| 2145 | 35 | Wild-type GIG |

Animals were young, approximately 6 months old but born at altitude, thus with lifelong exposure. Animals were separated by a cutoff of mPAP 39 mmHg into unaffected versus hypertensive ≥45 mmHg. DNA was tested for the EPAS1 double variant by Taqman assay. Each animal with one variant had both variants. Animals are designated as heterozygote G/A for carriers, homozygote G/G for wild type non-carriers, and A/A for homozygote carriers of the double variant. P<0.0023 Chi Square test.

TABLE 3

26 of 27 genes known to be upregulated by HIFs are increased in cattle with HAPH and EPAS1 variant compared to unaffected non-carrier high altitude controls

| Gene Symbol | Gene Title | Fold Change | T-Test |
|---|---|---|---|
| ANG | angiogenin, ribonuclease, RNase A family, 5 | 1.4 | 2.4E-02 |
| BNIP3L | BCL2/adenovirus E1B 19 kDa interacting protein 3-like | 1.4 | 1.0E-03 |
| CADM1 | cell adhesion molecule 1 | 1.8 | 3.6E-04 |
| CD59 | CD59 molecule, complement regulatory protein | 1.9 | 2.6E-03 |
| CYB5A | CYB5 protein | 1.4 | 1.5E-04 |
| DUSP1 | dual specificity phosphatase 1 | 1.6 | 1.2E-02 |
| ECE1 | endothelin converting enzyme 1 | 1.4 | 5.5E-05 |
| FOS | FBJ murine osteosarcoma viral oncogene homolog | 1.6 | 2.0E-02 |
| GADD45B | growth arrest and DNA-damage-inducible, beta | 1.5 | 2.2E-02 |
| GYS1 | glycogen synthase 1 (muscle) | 1.4 | 2.0E-04 |
| ISG20 | interferon stimulated exonuclease gene 20 kDa | 1.8 | 2.3E-02 |
| JUN | jun oncogene | 1.7 | 5.8E-05 |
| KLF6 | Kruppel-like factor 6 | 1.7 | 3.3E-03 |
| NDRG1 | N-myc downstream regulated 1 | 1.6 | 1.1E-04 |
| NFIL3 | nuclear factor, interleukin 3 regulated | 2.5 | 7.2E-04 |
| PAM | peptidylglycine alpha-amidating monooxygenase | 1.7 | 1.8E-05 |
| PFKFB3 | 6-phosphofructo-2-kinase/fructose-2,6-biphosphatase 3 | 1.6 | 7.2E-03 |
| PLAC8 | placenta-specific 8 | 1.9 | 2.5E-02 |
| PLAUR | plasminogen activator, urokinase receptor | 1.5 | 1.9E-03 |
| S100A4 | S100 calcium binding protein A4 | 1.3 | 3.5E-03 |
| SAT1 | spermidine/spermine N1-acetyltransferase 1 | 1.5 | 8.3E-03 |
| SCARB1 | scavenger receptor class B, member 1 | 1.4 | 3.6E-04 |
| SERPINE1 | serpin peptidase inhibitor, clade E | 1.9 | 6.0E-06 |
| SORL1 | sortilin-related receptor, L(DLR class) A repeats-containing | 1.6 | 6.6E-04 |
| TXNIP | thioredoxin interacting protein | 1.3 | 5.2E-03 |
| Vldlr | very low density lipoprotein receptor | 2.3 | 3.4E-07 |
| ZMYND8 | Zinc finger, MYND-type containing 8 | −1.5 | 7.1E-03 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

Alderborn et al., Genome Research 10(8):1249-1258 (2000).
American Lung Association. State-by-State Lung Disease Trend Report, April (2001).
Anand et al., Thorax 41: 696-700, (1986).
Archer et al., Circ Res., 95:308-18, (2004).
Atwood et al., Chest, 126:72S-77S, (2004).
Ausubel et al., Current Protocols in Molecular Biology, John Wiley & Sons, N.Y. (2003).
Beall et al., Proc Natl Acad Sci USA, June: 25(107):11459-64, (2010).
Berge et al., In: Proc. 10$^{th}$ World Congr. Appl. Livestock Prod. 2014., sas.org/docs/default-source/wcgalp-posters/430_paper_9946_manuscript_1110_0.pdf?sfvrsn=2, 2014.
Chaouat et al., Chest., 109, 380-386, (1996).
Chen et al., Genome Research 9(5):492-498 (1999).
Cheng et al., Proteins, 62 (4): 1125-1132, (2006).
Church and Gilbert, Proc. Natl. Acad. Sci. USA 81:1991-1995 (1988).
Cockrum et al., Proceedings World Congress Applied to Livestock Production. Vancouver, BC, Canada, Aug. 17-22, (2014).
Cotton et al., Proc. Natl. Acad. Sci. USA 85:4397-4401 (1985).
Darling and Holt, Biometrics., 55:55-64, (1999).
Das et al., Am J Physiol Lung Cell Mol Physiol., 282: L976-L986, (2002).
Davie et al., Am J Physiol Lung Cell Mol Physiol., 286: L668-L678, (2004).
Droma et al., Circ., 106:826-830, (2002).
Eckert et al., PCR Methods and Applications 1:17 (1991).
Eddahibi et al., Circulation, 108:1839-44, (2003).
Edwards and Li, Genetic Epidemiology, 36:472-479, (2012).
Elvidge et al., J Bio Chem., 281:15215-15226, (2006).
Fagan and Weil, Potential genetic contributions to control of the pulmonary circulation and ventilation at high altitude. In Press.
Fagan et al., Am J Physiol Lung Cell Mol Physiol., 287: L656-L664, (2004).
Fanburg et al., Clin in Chest Med, (1994).
Fishman, The American Physiological Society., pg93-165.47, (1985).
Flavell et al., Cell 15:25 (1978).
Foletta et al., J Cell Biol., 162:1089-98, (2003).
Gale et al., Blood, 112f:919-921, (2008).
Geever et al., Proc. Natl. Acad. Sci. USA 78:5081 (1981).

Gjermundson, Angus J (November): 47-50, (2000).
Gjermundson, *Angus J.*, (November): 47-50, (2000).
Glover and Newsom, Brisket Disease (Dropsy of High Altitude). Colorado Agricultural Experiment Station. 204 Preliminary Report, 3-24 (1915).
Glover and Newsom, *Colorado Agricultural Experiment Station.*, 204 Preliminary Report, 3-24, 1915.
Grover et al., *Am Heart J* 66: 1, (1963 a).
Grover et al., *J Appl Physiol.*, 18: 567-574, (1963b).
Grover et al., *J Appl Physiol.*, 18: 567-574, (1965).
Grover et al., *The American Physiological Society*, Vol 111, Part 1. pg 103-136, (1983).
Grover, Failing hearts at high altitude. In: Attitudes on Altitude, edited by Reeves J T and Grover R F. Boulder, Colo.: University Press of Colorado, p. 1-24, (2001).
Grover, *Ann NY Acad Sci.*, 127:632-9, (1965).
Grover, In: *Attitudes on Altitude*, edited by Reeves, J T and Grover, R F. Boulder, Colo.: University Press of Colorado, p. 1-24, (2001).
Groves et al., *J Appl Physiol.*, 74: 312-318, (1993).
Guatelli et al., *Proc. Nat. Acad. Sci. USA* 87:1874 (1990).
Hanaoka et al., *Chest*, 123:54-58, (2003).
Heath and William, Man at High Altitude. Churchill Livingstone, Edinburgh and New York, 892:1158-1163, (1981).
Hickey and Simon, *Curr Top Dev Biol.*, 76:217-257, (2006).
Hickey et al., *J Cin Invest.*, 120(3):827-39, (2010).
Holt and Callan, *Vet Clin Food Anim.*, 23:575-96, (2007).
Hultgren and Grover, *Annu Rev Med.*, 19: 119-152, (1968).
Jensen et al., *J Am Vet Med Assoc.*, (1976).
Jernigan et al., Am J Physiol Lung Cell Mol Physiol, 287:L1220-29, (2004).
Kuriyama and Wagner, *J Appl Physiol.*, 51: 1251-1256, (1981).
Kwoh et al., Proc. Natl. Acad. Sci. USA 86:1173 (1989).
Landegren et al., Science 241:1077 (1988).
MacNee, *State of the Art. Am J Pulm Crit Care Med.*, 150:833-45, (1994).
Maggiorini and Leon-Velarde, High-altitude pulmonary hypertension: pathophysiological entity to different diseases., 22:1019-1025, (2003).
Maniatis et al., Proc. Natl. Acad. Sci. USA 99:2228-2233 (2002).
Mattila et al., Nucleic Acids Res. 19:4967 (1991).
Mauban et al., *J Appl Physiol.*, 98:415-20, (2005).
McPherson et al., PCR Basics: From Background to Bench, Springer-Verlag, (2000).
Moore et al., In: *Oxygen Sensing: Molecule to Man*, edited by Lahiri S. New York: Kluwer Academic/Plenum Publishers, p. 45-62, (2000).
Morrell et al., Preliminary identification of genetic loci associated with high altitude pulmonary hypertension by association mapping. Abstract, A842. ATS International Conference (2003).
Mortimer et al., Pharmacology & Therapeutics., 101:183-192, (2004).
Morton et al., Proc. Natl. Acad. Sci. USA 98(9):5217-21 (2001).
Moudgil et al., *J Appl Physiol.*, 98:390-403, (2005).
Myers et al., Science 230:1242 (1985).
Nagaoka et al., *Am J Physiol Lung Cell Mol Physiol*, 287: L665-L672, (2004).
Nath and Johnson, Biotechnic. Histochem. 73(1):6-22 (1998).
National Center for Health Statistics. Deaths: Final Data for 1999, 49 (8), (2001).
Neary, et al., *J Vet Diag Invest*, 25:210-218, (2013).
Newman et al., *Pulm Circ.*, (4):462-469, (2011).
Nielsen et al., Bioconjugate Chemistry, The American Chemical Society, 5:1 (1994).
Nocturnal Oxygen Therapy Trial Group. Ann Intern Med, 93:391-398, (1980).
Orita et al., Proc. Natl. Acad. Sci. USA 86:2766-2770 (1989).
Palevsky and Fishman, *JAMA.*, 263:2347-2354, (1990).
Pasha and Newman, *Chest*, 137; 13S-19S, (2010).
Penaloza and Arias-Stella, *Circ.*, 115:1132-1146, (2007).
Percy et al., *N Eng J Med.*, 358:162-168, (2008).
Prince et al., Genome Res. 11:152-162 (2001).
Pulmonary Circulation: Diseases and their treatment. Eds Peacock A J and Rubin L J., Arnold Hodder Publisher, London, (2004).
Rabinovitch, *Chest*, 128(s):641-46, (2005).
Raca et al., Genet Test 8(4):387-94 (2004).
Reeves and Grover, *J Appl Physiol.*, 98:384-389, (2004).
Reeves, *Am J Resp Crit Care Med* 166: 1537-1538, (2002).
Remillard and Yuan, *High J Alt Med Biol.*, 56:133-46, (2005).
Rhodes, *J Appl Physiol.*, 98:1092-1100, (2005).
Richards, *Am Rev Resp Dis.*, 94:691-702, (1966).
Rupert and Hochachka, *High Alt Med Biol* 2: 235-256, (2001).
Saiki et al., Nature 324:163-166 (1986).
Sanger et al., Proc. Natl. Acad. Sci. USA 74:5463-5467 (1977).
Schafer et al., Nat. Biotechnol. 15:33-39 (1995).
Semenza, *Cell*, 148(3):3990408, (2012).
Sheffield et al., Proc. Natl. Acad. Sci. USA 86:232-236 (1989).
Shimoda and Semenza, *Am J Resp Crit Care Med.*, 183: 152-156, (2011).
Shirley et al., *J Anim Sci.*, 86(4):815-9, (2008).
Short et al., *Am J Physiol Cell Physiol.*, 286: C416-C425, (2004).
Simonson et al., *Science*, 329:72-75, (2010).
Stenmark and McMurtry, *Circ Res.*, 22; 97:95-98, (2005).
Stoneking et al., Am. J. Hum. Genet. 48:370-382 (1991).
Sylvester, *Circ Res.*, 88:1228-9, (2001).
Tan et al., *J Biol Chem*, 288:17134-17144, (2013).
Tapper et al., Proc. Natl. Acad. Sci. USA 102(33):11835-11839 (2005).
The International HapMap Consortium, Nature 426:789-796 (2003).
The International HapMap Consortium, Nature 437:1299-1320 (2005).
Tucker et al., *Am J Physiol.*, 228:762-767, (1975).
U.S. Pat. No. 4,683,195
U.S. Pat. No. 4,683,202
U.S. Pat. No. 5,288,644
U.S. Pat. No. 5,491,224
U.S. Pat. No. 5,776,688
U.S. Pat. No. 5,800,998
U.S. Patent Publication No. 2004/0014095
Underhill et al., Genome Res. 7:996-1005 (1997).
von Euler and Liljestrand, *Acta Physiol Scand.*, 12:301-320, (1946).
Wang et al., *Am J Respir Cell Mol Biol.*, 29:465-71, (2003).
Ward and Robertson, *Am J Physiol Lung Cell Mol Physiol.*, 289:2-4, (2005).
Weir et al., *Cardiovascular Res.*, 8; 745-49, (1974).
Weissmann et al., *Am J Physiol Lung Cell Mol Physiol.*, 281:L314-7, (2001).
Weitzenblum et al., *Thorax.*, 36:752-758, (1981).
Wheeless et al., Cytometry 17:319-326 (1994).

Will and Bisgard, *Prog Respir Res* 9: 138-143, (1975).
Will et al., *J Appl Physiol* 38: 495-498, (1975).
Will et al., *J Appl Physiol.*, 38:491-494, (1975).
WO 99/57318
Wolin et al., *Am J Physiol Lung Cell Mol Phsiol.*, 289:159-73, (2005).
Wood, *Br Heart J.*, 4:557-70, (1958).
Wu and Wallace, Genomics 4:560 (1989).
Xin et al., *Science,* 329:75-78, (2010).

What is claimed is:

1. A method for transporting cattle, comprising,
   a) subjecting a nucleic acid-containing sample from a head of cattle to nucleic acid sequence analysis;
   b) detecting the nucleotide present at position 1816 and/or 1828 in exon 12 of the bovine EPAS1 gene; and
   c) transporting the head of cattle
      wherein the head of cattle is transported out of a high or intermediate altitude environment when the cattle has an A transition at position 1816 and/or an A transition at position 1828 in exon 12 of the bovine EPAS1 gene and
      the head of cattle is transported from a low altitude environment to an intermediate or high altitude environment if the cattle does not have an A transition at position 1816 or an A transition at position 1828 in exon 12 of the bovine EPAS1 gene.

2. The method of claim 1, further comprising subjecting said nucleic acid-containing sample to analysis of expression for one or more of:
   Angiogenin, ribonuclease, Rnase A family, 5
   BCL2/adenovirus E1B 19 kDa interacting protein 3-like
   Cell adhesion molecule 1
   CD59 molecule, complement regulatory protein
   CYB5 protein
   Dual specificity phosphatase 1
   Endothelin converting enzyme 1
   FBJ murine osteosarcoma viral oncogene homolog
   Growth arrest and DNA-damage-inducible, beta
   Glycogen synthase 1 (muscle)
   Interferon stimulated exonuclease gene 20 kDa
   Jun oncogene
   Kruppel-like factor 6
   N-myc downstream regulated 1
   Nuclear factor, interleukin 3 regulated
   Peptidylglycine alpha-amidating monooxygenase
   6-phosphofructo-2-kinase/fructose-2,6-biphosphatase 3
   Placenta-specific 8
   Plasminogen activator, urokinase receptor
   S100 calcium binding protein A4
   Spermidine/spermine N1-acetyltransferase 1
   Scavenger receptor class B, member 1
   Serpin peptidase inhibitor, clade E
   Sortilin-related receptor, L(DLR class) A repeats-containing
   Thioredoxin interacting protein
   Very low density lipoprotein receptor
   and
   Zinc finger, MYND-type containing 8.

3. The method of claim 1, wherein said nucleic acid containing sample is a DNA sample or an RNA sample.

4. The method of claim 1, wherein said nucleic acid containing sample is a tissue, saliva, serum, blood, semen, ova, hair or a mucosal cell.

5. The method of claim 1, wherein said sequence analysis comprises PCR, primer extension, site specific amplification, site specific hybridization, site specific cleavage, ligation, pyrosequencing, SNP microarray, minisequencing, RNA seq, real time sequencing, ion or torrent pH sensing.

6. The method of claim 1, wherein said head of cattle is *Bos taurus* or *Bos primigenius*.

7. A method of breeding cattle, comprising,
   a) subjecting a nucleic acid-containing sample from a head of cattle to nucleic acid sequence analysis;
   b) analyzing the nucleotide present at positions 1816 and/or 1828 in exon 12 of the bovine EPAS1 gene;
   c) detecting a G allele at position 1816 in exon 12 of the bovine EPAS1 gene and/or a G allele present at position 1828 in exon 12 of the bovine EPAS1 gene; and
   d) breeding the head of cattle with a G allele at position 1816 in exon 12 of the bovine EPAS1 gene and/or a G allele present at position 1828 in exon 12 of the bovine EPAS1 gene.

8. The method of claim 7, further comprising subjecting said nucleic acid-containing sample to analysis of expression for one or more of:
   Angiogenin, ribonuclease, Rnase A family, 5
   BCL2/adenovirus E1B 19 kDa interacting protein 3-like
   Cell adhesion molecule 1
   CD59 molecule, complement regulatory protein
   CYB5 protein
   Dual specificity phosphatase 1
   Endothelin converting enzyme 1
   FBJ murine osteosarcoma viral oncogene homolog
   Growth arrest and DNA-damage-inducible, beta
   Glycogen synthase 1 (muscle)
   Interferon stimulated exonuclease gene 20 kDa
   Jun oncogene
   Kruppel-like factor 6
   N-myc downstream regulated 1
   Nuclear factor, interleukin 3 regulated
   Peptidylglycine alpha-amidating monooxygenase
   6-phosphofructo-2-kinase/fructose-2,6-biphosphatase 3
   Placenta-specific 8
   Plasminogen activator, urokinase receptor
   S100 calcium binding protein A4

Spermidine/spermine N1-acetyltransferase 1
Scavenger receptor class B, member 1
Serpin peptidase inhibitor, clade E
Sortilin-related receptor, L(DLR class) A repeats-containing
Thioredoxin interacting protein
Very low density lipoprotein receptor
and
Zinc finger, MYND-type containing 8.

9. The method of claim 7, wherein said nucleic acid containing sample is a DNA sample or an RNA sample.

10. The method of claim 7, wherein said nucleic acid containing sample is a tissue, saliva, serum, blood, semen, ova, hair or a mucosal cell.

11. The method of claim 7, wherein said sequence analysis comprises PCR, primer extension, site specific amplification, site specific hybridization, site specific cleavage, ligation, pyrosequencing, SNP microarray, minisequencing, RNA seq, real time sequencing, ion or torrent pH sensing.

12. The method of claim 7, wherein said head of cattle is *Bos taurus* or *Bos primigenius*.

\* \* \* \* \*